(12) United States Patent
Bourett et al.

(10) Patent No.: US 9,150,625 B2
(45) Date of Patent: Oct. 6, 2015

(54) CHLOROPLAST TRANSIT PEPTIDES AND METHODS OF THEIR USE

(75) Inventors: Timothy M. Bourett, Middletown, DE (US); Gary C. Chun, Newark, DE (US); Albert Laurence Lu, Newark, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 466 days.

(21) Appl. No.: 13/467,329

(22) Filed: May 9, 2012

(65) Prior Publication Data

US 2012/0304336 A1 Nov. 29, 2012

Related U.S. Application Data

(60) Provisional application No. 61/488,952, filed on May 23, 2011.

(51) Int. Cl.
  *C07K 14/415* (2006.01)
  *C12N 15/82* (2006.01)
(52) U.S. Cl.
  CPC .......... *C07K 14/415* (2013.01); *C12N 15/8221* (2013.01)
(58) Field of Classification Search
  None
  See application file for complete search history.

(56) References Cited

U.S. PATENT DOCUMENTS

| 5,717,084 | A | 2/1998 | Herrera-Estrella et al. |
| 6,489,542 | B1 | 12/2002 | Corbin et al. |
| 7,064,249 | B2 | 6/2006 | Corbin et al. |
| 2011/0268865 | A1* | 11/2011 | Kebeish et al. ............... 426/622 |

FOREIGN PATENT DOCUMENTS

WO WO 2005/123929 A2 12/2005

OTHER PUBLICATIONS

Apt, K., et al., "In vivo characterization of diatom multipartite plastid targeting signals," *Journal of Cell Science*, 2002, vol. 115(21), pp. 4061-4069.
Bruce, Barry D., "Chloroplast transit peptides: structure, function and evolution," *trends in Cell Biology*, 2000, vol. 10(10), pp. 440-447.
Bruce, Barry D., "The paradox of plastid transit peptides: conservation of function despite divergence in primary structure," *Biochimica et Biophysica Acta*, 2001, vol. 1541(1-2), pp. 2-21.
Bionda, T., et al., "Chloroplast Import Signals: The Length Requirement for Translocation In Vitro and In Vivo," *Journal of Molecular Biology*, 2010, vol. 402(3), pp. 510-523.
Lee, D., et al., "Functional Characterization of Sequence Motifs in the Transit Peptide of *Arabidopsis* Small Subunit of Rubisco," *Plant Physiol*, 2006, vol. 140(2), pp. 466-483.
Miras, S., et al., "Non-canonical Transit Peptide for Import into the Chloroplast," *The Journal of Biological Chemistry*, 2002, vol. 277(49), pp. 47770-47778.

\* cited by examiner

*Primary Examiner* — Brent T Page
(74) *Attorney, Agent, or Firm* — E I Du Pont De Nemours and Co

(57) ABSTRACT

Methods and compositions are provided for targeting a polypeptide of interest to a chloroplast. Recombinant polynucleotides comprising a nucleotide sequence encoding a chimeric chloroplast transit peptide (CTP) operably linked to a heterologous polynucleotide of interest are provided. In specific embodiments, the chimeric CTP comprises an N-terminal domain operably linked to a central domain operably linked to a C-terminal domain of a CTP to form a chimeric chloroplast transit peptide having CTP activity. Recombinant polypeptides encoding the same, as well as, cells, plant cells, plants and seeds are further provided which comprise the recombinant polynucleotides. Methods of use of the various sequences are also provided.

18 Claims, 2 Drawing Sheets

Figure 1

Strategy for CTP Development

| CTP framework | Uncharged N-terminus | | R rich C-terminus Amphipathic helix |
|---|---|---|---|
| msCTP1 | OsdXP | ssRUBISCO (Zm) | β-Gluc |
| msCTP2 | NADP | OsSOD | Ds-soluble starch |
| msCTP3 | OsNADP-malic enzyme | OsPHD Aldolase 2 | TRX |
| msCTP4 | NADP/OsNADP-malic enzyme | ssRUBISCO (Zm) | Ds. sol. starch/TRX |
| msCTP5 | NADP/OsNADP | OsAPxOS/ssRUBISCO | OsSOD/OsPGDK |
| msCTP6 | Most freq AA | Most freq AA | Most freq AA |
| msCTP7 | Most freq AA | Most freq AA | Most freq AA |

CHLOROPLAST TRANSIT PEPTIDES AND METHODS OF THEIR USE

CROSS-REFERENCE TO RELATED APPLICATIONS

This application claims the benefit of U.S. Provisional Application No. 61/488,952, filed May 23, 2011, which is hereby incorporated herein in its entirety by reference.

REFERENCE TO SEQUENCE LISTING

The sequence listing submitted Sep. 30, 2013 as a text file named 36446_0050U1_Revised_Sequence_Listing.txt, created on Sep. 30, 3013, and having a size of 43,924 bytes is hereby incorporated by reference pursuant to 37 C.F.R. 1.52 (e)(5).

FIELD OF THE INVENTION

This invention is in the field of molecular biology. More specifically, this invention pertains to targeting sequences of interest to a chloroplast by employing novel chloroplast transit peptides.

BACKGROUND OF THE INVENTION

Plastids are a heterogeneous family of organelles found ubiquitously in plants and algal cells. Most prominent are the chloroplasts, which carry out such essential processes as photosynthesis and the biosynthesis of fatty acids as well as of amino acids. Chloroplasts are complex organelles composed of six distinct suborganellar compartments: three different membranes (the two envelope membranes and the internal thylakoid membranes) and three compartments (the inner-membrane space of the envelope, the stroma and the thylakoid lumen). More than 98% of all plastid proteins are translated on cytosolic ribosomes. Such proteins are posttranslationally targeted to and imported into the organelle. For a review, see, Jarvis et al. (2008) *New Phytologist* 179:257-285. Such translocation is mediated by multi-protein complexes in the outer and inner envelope membranes called TOC (Translocon at the Outer envelope membrane of Chloroplasts) and TIC (Translocon at the Inner envelope membrane of Chloroplasts). See, Soll et al. (2004) *Nature Reviews. Molecular Cell Biology* 5:198-208, Bedard et al. (2005) *Journal of Experimental Botany* 56:2287-2320, Kessler et al. (2006) *Traffic* 7:248-257, and Smith et al. (2006) *Canadian Journal of Botany* 84:531-542. Once the chloroplast precursor enters the stroma, the transit peptide is cleaved off, leaving the remaining part of the protein to take on its final conformation or engage one of a number of different sorting pathways. See, Keegstra et al. (1999) *Plant Cell* 11:557-570, Jarvis et al. (2004) and Gutensohn et al. (2006) *Journal of Plant Physiology* 163:333-347.

Methods and compositions are needed to allow heterologous polypeptides to be targeted to the chloroplast.

BRIEF SUMMARY OF THE INVENTION

Methods and compositions are provided for targeting a polypeptide of interest to a chloroplast. Recombinant polynucleotides comprising a nucleotide sequence encoding a chimeric chloroplast transit peptide (CTP) operably linked to a heterologous polynucleotide of interest are provided. In specific embodiments, the chimeric CTP comprises an N-terminal domain operably linked to a central domain operably linked to a C-terminal domain of a CTP to form a chimeric chloroplast transit peptide having CTP activity. Recombinant polypeptides encoding the same, as well as, cells, plant cells, plants and seeds are further provided which comprise the recombinant polynucleotides. Methods of use of the various sequences are also provided.

BRIEF DESCRIPTION OF THE DRAWINGS

FIG. 1 provides a strategy for developing the recombinant chloroplast transit peptides provided herein. The origin of each segment of the CTP framework for the recombinant chloroplast transit peptides is provided.

DETAILED DESCRIPTION OF THE INVENTION

Figure 2:
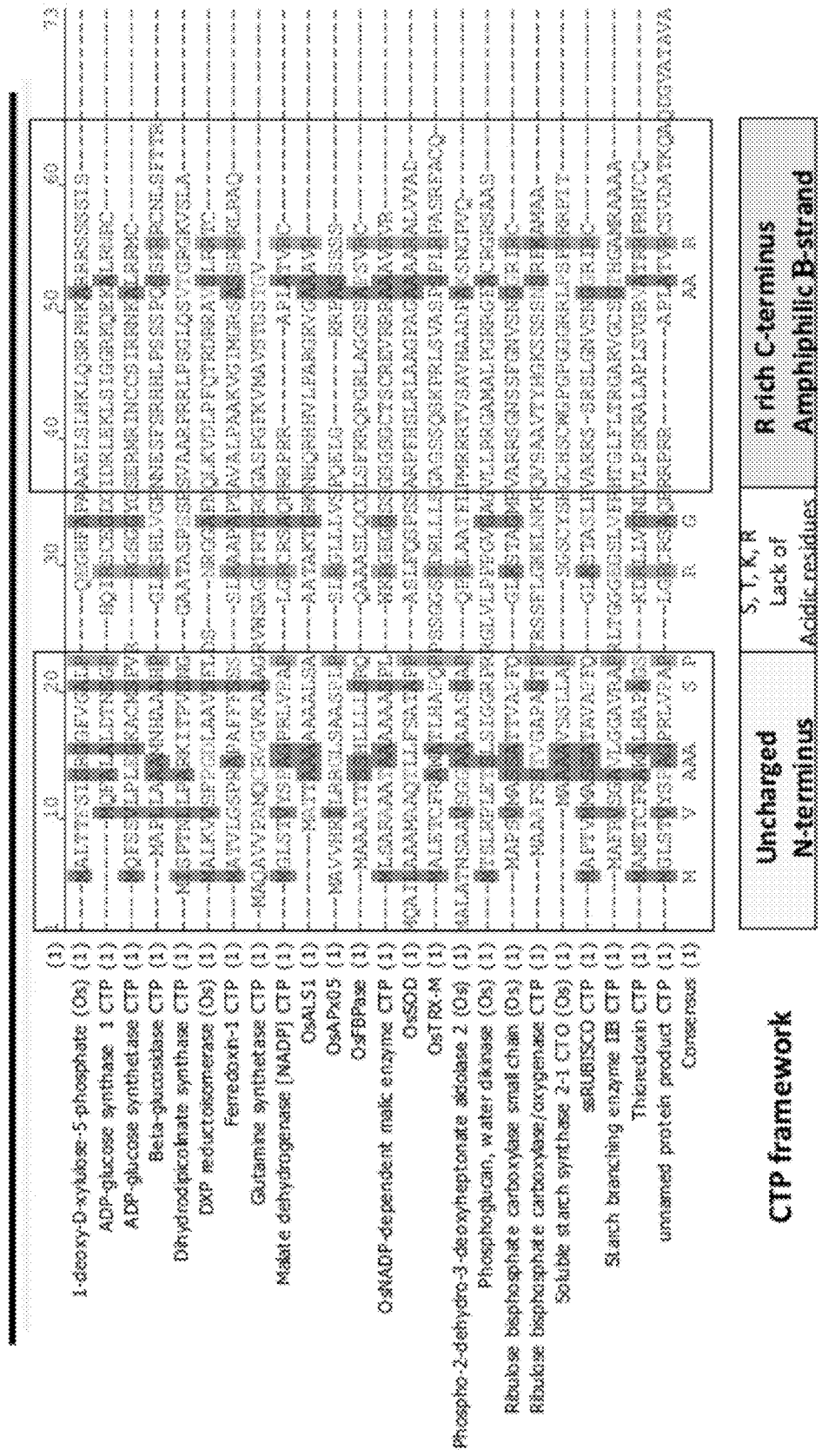
FIG. 2 provides an amino acid alignment of chloroplast transit peptides from various monocot plants. The most frequent amino acids are highlighted. Starting from the top, the sequences are identified as SEQ ID NO:13, SEQ ID NO:44, SEQ ID NO:45, SEQ ID NO:21, SEQ ID NO:46, SEQ ID NO:47, SEQ ID NO:48, SEQ ID NO:49, SEQ ID NO:22, SEQ ID NO:50, SEQ ID NO:18, SEQ ID NO:51, SEQ ID NO:16, SEQ ID NO:14, SEQ ID NO:52, SEQ ID NO:17, SEQ ID NO:19, SEQ ID NO:53, SEQ ID NO:54, SEQ ID NO:15, SEQ ID NO:20, SEQ ID NO:55, SEQ ID NO:23, SEQ ID NO:56, SEQ ID NO:11.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Compositions

A. Overview

In the production of transgenic plants it is often useful to direct foreign proteins to specific subcellular locations, e.g., the plastid, vacuole, mitochondria, or ER. When the gene is translated, the resulting protein has the transit peptide fused to the amino terminus of the protein of interest, and thus the protein is directed to the desired subcellular compartment. Of particular interest is the identification of transit peptides that will direct transport to a plastid. As used herein, a "plastid" refers to an organelle present in plant cells that stores and manufactures chemical compounds used by the cell, such as starch, fatty acids, terpenes, and that has been derived from a proplastid. Thus, plastids of plants typically have the same genetic content. Plastids include chloroplasts, which are responsible for photosynthesis, amyloplasts, chromoplasts, statoliths, leucoplasts, elaioplasts, and proteinoplasts. Plastids contain photosynthetic machinery and many additional biosynthetic enzymes including those leading to the production of fatty acids, amino acids, carotenoids, terpenoids, and starch. Thus, there is a need for the ability to target polypeptides of interest to plastids to modulate or alter the physiological processes that occur within these organelles. In addition, some polypeptides are toxic when expressed recombinantly in the cytoplasm. Because plastids are subcompartments, it is possible to target polypeptides of interest to the plastids to sequester them from the cytoplasm, and thus allow for higher expression levels. Furthermore, expression of recombinant polypeptides in plastids may facilitate isolation of the polypeptide for various applications. As discussed in further detail herein, novel chimeric chloroplast transit peptides are provided which can be used in plastid targeting.

The compositions provided herein include recombinant polynucleotides comprising a nucleotide sequence encoding a novel chloroplast transit peptide (CTP) operably linked to a nucleotide sequence encoding a polypeptide of interest. The CTP-encoding sequences disclosed herein, when assembled within a DNA construct such that the CTP-encoding sequence is operably linked to a nucleotide sequence encoding the polypeptide of interest, facilitate co-translational or post-translational transport of the peptide of interest to the chloroplast of a plant cell.

B. Chloroplast Transit Peptides

Chloroplasts are organelles found in plant cells and eukaryotic algae that conduct photosynthesis. The chloroplast is a complex cellular organelle composed of three membranes: the inner envelope membrane, the outer envelope membrane, and the thylakoid membrane. The membranes together enclose three aqueous compartments termed the intermediate space, the stroma, and the thylakoid lumen. While chloroplasts contain their own circular genome, many constituent chloroplast proteins are encoded by the nuclear genes and are cytoplasmically-synthesized as precursor forms which contain N-terminal extensions known as chloroplast transit peptides (CTPs). As used herein, the term "chloroplast transit peptide" or "CTP" refers to the N-terminal portion of a chloroplast precursor protein and influences the recognition of the chloroplast surface and mediates the post-translational translocation of pre-proteins across the chloroplast envelope and into the various subcompartments within the chloroplast (e.g. stroma, thylakoid and thylakoid membrane). Thus, as used herein, a polypeptide having "CTP activity" comprises a polypeptide which when operably linked to the N-terminal region of a protein of interest facilitates translocation of the polypeptide of interest to the chloroplast.

Assays to determine the efficiency by which the CTP sequences provided herein target a protein of interest to a chloroplast are known. See, for example, Mishkind et al. (1985) *J. of Cell. Biol.* 100:226-234, which is herein incorporated by reference in its entirety. A reporter gene such as glucuronidase (GUS), chloramphenicol acetyl transferase (CAT), or green fluorescent protein (GFP) is operably linked to the CTP sequence. This fusion is placed behind the control of a suitable promoter, ligated into a transformation vector, and transformed into a plant or plant cell. Following an adequate period of time for expression and localization into the chloroplast, the chloroplast fraction is extracted and reporter activity assayed. The ability of the CTP sequences to target and deliver the reporter protein to the chloroplast can be compared to other known CTP sequences. See, de Castro Silva Filho et al. (1996) *Plant Mol. Biol.* 30: 769-780. Protein import can also be verified in vitro through the addition of proteases to the isolated chloroplast fraction. Proteins which were successfully imported into the chloroplast are resistant to the externally added proteases whereas proteins that remain in the cytosol are susceptible to digestion. Protein import can also be verified by the presence of functional protein in the chloroplast using standard molecular techniques for detection, by evaluating the phenotype resulting from expression of a chloroplast targeted protein, or by microscopy.

a. Chimeric Chloroplast Transit Peptides

Recombinant polynucleotides encoding a chimeric CTP operably linked to a heterologous polynucleotide of interest are provided herein. The chimeric CTPs comprise heterologous domains of known or predicted CTPs which, when operably linked, have CTP activity.

CTPs have a preference for hydroxylated amino acids (S, T, P) and lack acidic residues. They share a common structural framework comprising an uncharged N-terminal region ("N-terminal domain"), a central region ("central domain"), and a basic arginine-rich amphipathic C-terminal region ("C-terminal domain"). The domain framework structure of CTPs is provided in FIG. 1. Thus, the CTPs provided herein comprise 3 domains, an N-terminal domain, a central domain and a C-terminal domain.

As used herein, "N-terminal domain" refers to an N-terminal hydrophobic region of a CTP comprising uncharged amino acids. The N-terminal domain can comprise at least 5-10, 5-11, 5-12, 5-13, 5-14, 5-15, 5-16, 5-17, 5-18, 5-19, 5-20 or more amino acids from the N-terminus of a CTP sequence generally beginning with MA and ending in G/P. The N-terminal domain can comprise additional sequences, such as linker sequences, such that when operably linked to a central domain and C-terminal domain reconstitutes a CTP having CTP activity.

A "central domain" as used herein, refers to a central region of a CTP comprising an amino acid sequence lacking acidic amino acids and enriched in serine, threonine, lysine and arginine. The central domain can comprise at least 4-5, 4-6, 4-7, 4-8, 4-9, 4-10, 4-11, 4-12, 4-13, 4-14, 4-15 or more amino acids from the central region of a CTP sequence. The central domain can also comprise additional sequences such as linker sequences, such that when operably linked to an N-terminal domain and a C-terminal domain reconstitutes a CTP having CTP activity.

As used herein, "C-terminal domain" refers to a C-terminal region of a CTP comprising an amino acid sequence which is basic, arginine-rich and predicted to form an amphiphilic beta strand. The C-terminal domain can comprise at least 5-10, 5-15, 5-16, 5-17, 5-18, 5-19, 5-20, 5-21, 5-22, 5-23, 5-24, 5-25, 5-26, 5-27, 5-28, 5-29, 5-30 or more amino acids from the C-terminal region of a CTP sequence. The C-terminal domain can comprise additional sequences such as linker sequences, such that when operably linked to an N-terminal domain and a central domain reconstitutes a CTP having CTP activity.

Non-limiting examples of domains for various CTPs are set forth in SEQ ID NOS: 24-43 and summarized in Table 4.

A "chimeric CTP" provided herein comprises an N-terminal domain, a central domain, and a C-terminal domain from any CTP in which the sequence of at least one of the domains is heterologous to the sequence of the other domains and whereby the domains, when operably linked, reconstitute a CTP with CTP activity. As used herein the term "chimeric" refers to a sequence having two or more heterologous sequences linked together. As used herein, "heterologous" in reference to a sequence is a sequence that originates from a foreign species, for example, from a different CTP, or, if from the same species, is substantially modified from its native form in composition and/or genomic locus by deliberate human intervention. For example, a heterologous domain is intended at least one of the CTP domains is not from the same CTP, but could be from a different CTP of the same plant species or a different plant species. The chimeric CTPs provided herein can vary in length from about 30, 35, 40, 45, 50, 51, 52, 53, 54, 55, 56, 57, 58, 59, 60, 61, 62, 63, 64, 65 or more amino acid residues in length such that it comprises an N-terminal domain, a central domain, and a C-terminal domain and retains CTP activity.

The domains of the chimeric CTPs can be from any known or predicted CTP sequence. For example, in some embodiments, the chimeric CTP can comprise, but is not limited to, an N-terminal domain, a central domain or a C-terminal domain from a CTP from *Oryza sativa* 1-deoxy-D xyulose-5-Phosphate Synthase, *Oryza sativa*-Superoxide dismutase, *Oryza sativa*-soluble starch synthase, *Oryza sativa*-NADP-dependent Malic acid enzyme, *Oryza sativa*-Phospho-2-dehydro-3-deoxyheptonate Aldolase 2, *Oryza sativa*-L-Ascorbate peroxidase 5, *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type or active variants thereof.

In specific, non-limiting, embodiments, the N-terminal domain of the chimeric CTP is from a CTP from *Oryza sativa* 1-deoxy-D xyulose-5-Phosphate Synthase, *Oryza sativa*-NADP-dependent Malic acid enzyme, *Zea Mays*-Malate dehydrogenase or active variants thereof. In other non-limiting embodiments, the central domain of the chimeric CTP is from a CTP from *Oryza sativa*-Superoxide dismutase, *Oryza sativa*-Phospho-2-dehydro-3-deoxyheptonate Aldolase 2, *Oryza sativa*-L-Ascorbate peroxidase 5, *Zea Mays* ssRUBISCO or active variants thereof. In yet other non-limiting embodiments, the C-terminal domain of the chimeric CTP is from a CTP from *Oryza sativa*-soluble starch synthase, *Oryza sativa*-Superoxide dismutase, *Oryza sativa*-Phosphoglucan water dikinase, *Zea Mays* Thioredoxin M-type, *Zea Mays*-beta-glucosidase or active variants thereof. Non-limiting examples of various CTPs, N-terminal domains, central domains and C-terminal domains of CTPs are set forth in SEQ ID NOS: 13-43.

In one specific embodiment, the chimeric CTP comprises the N-terminal domain from the *Oryza sativa* 1-deoxy-D xyulose-5-Phosphate Synthase CTP or an active variant thereof, the central domain from the *Zea Mays* ssRUBISCO CTP or an active variant thereof, and the C-terminal domain of the *Zea Mays*-beta-glucosidase CTP or an active variant thereof. In another specific embodiment, the chimeric CTP comprises the N-terminal domain from the *Zea Mays*-Malate dehydrogenase CTP or an active variant thereof, the central domain from the *Oryza sativa*-Superoxide dismutase CTP or an active variant thereof, and the C-terminal domain from the *Oryza sativa*-soluble starch synthase CTP or an active variant thereof. In yet another specific embodiment, the chimeric CTP comprises the N-terminal domain from the *Oryza sativa*-NADP-dependent Malic acid enzyme CTP or active variant thereof, the central domain from the *Oryza sativa*-Phospho-2-dehydro-3-deoxyheptonate Aldolase 2 CTP or an active variant thereof, and the C-terminal domain from the *Zea Mays* Thioredoxin M-type CTP or an active variant thereof.

Examples of chimeric CTPs are set forth in the amino acid sequences of SEQ ID NO: 1 (msCTP1) or an active variant or fragment thereof, SEQ ID NO: 2 (msCTP2) or an active variant or fragment thereof and SEQ ID NO: 3 (msCTP3) or an active variant or fragment thereof. The domain structures of the various CTPs provided herein are depicted in FIG. 1.

The chimeric CTPs provided herein can also comprise chimeric domains. As used herein, a "chimeric domain" refers to an N-terminal domain, central domain, or C-terminal domain of a CTP which comprises portions of two or more heterologous N-terminal domain, central domain, or C-terminal domain sequences fused together to reconstitute a complete domain. For example, a chimeric domain (i.e. a "chimeric N-terminal domain", "chimeric central domain" or "chimeric C-terminal domain") provided herein can comprise at least 2, 3, 4 or more heterologous CTP sequences fused together such that the chimeric domain, when incorporated in a chimeric CTP, has CTP activity.

In some embodiments, the chimeric CTPs can comprise at least 1, 2 or 3 chimeric domains. In specific embodiments, at least one portion of the chimeric N-terminal domain is from the N-terminal domain of the *Oryza sativa*-NADP-dependent Malic CTP, *Zea Mays*-Malate dehydrogenase CTP or active variants thereof. In other embodiments at least one portion of the chimeric central domain is from the central domain of the *Oryza sativa*-NADP-dependent Malic CTP, *Zea Mays*-Malate dehydrogenase CTP or active variants thereof. In yet other embodiments, at least one portion of the chimeric C-terminal domain is from the C-terminal domain of the *Oryza sativa*-soluble starch synthase CTP, *Zea Mays* Thioredoxin M-type CTP, *Oryza sativa*-Superoxide dismutase CTP, *Oryza sativa*-Phosphoglucan water dikinase CTP or active variants thereof.

In a specific embodiment, the chimeric CTP comprises a chimeric N-terminal domain comprising a portion of the N-terminal domain from the *Zea Mays*-Malate dehydrogenase CTP fused in frame to a portion of the N-terminal domain of the *Oryza sativa*-NADP-dependent Malic acid enzyme CTP, a central domain from the *Zea Mays* ssRUBISCO CTP, and a chimeric C-terminal domain comprising a portion of the C-terminal domain from the *Oryza sativa*-soluble starch synthase CTP fused in frame to a portion of the C-terminal domain from the *Zea Mays* Thioredoxin M-type CTP, wherein the chimeric CTP has CTP activity.

In another specific embodiment, the chimeric CTP comprises a chimeric N-terminal domain comprising a portion of the *Zea Mays*-Malate dehydrogenase CTP fused in frame to a portion of the *Oryza sativa*-NADP-dependent Malic acid enzyme CTP, a chimeric central domain comprising a portion of the *Oryza sativa*-L-Ascorbate peroxidase 5 CTP fused in frame to a portion of the *Zea Mays* ssRUBISCO CTP, and a chimeric C-terminal domain comprising a portion of the *Oryza sativa*-Superoxide dismutase CTP fused in frame to a portion of the *Oryza sativa*-Phosphoglucan water dikinase CTP, wherein the chimeric CTP has CTP activity.

Exemplary CTPs comprising chimeric domains are set forth in the amino acid sequences of SEQ ID NO:4 (msCTP4) or an active or fragment variant thereof and SEQ ID NO:5 (msCTP5) or an active variant or fragment thereof. Examples of chimeric CTP domain structures are provided in FIG. 1.

b. Consensus Chloroplast Transit Peptides

While the chimeric CTPs described in the previous section employed a domain approach for CTP design, it is recognized that other approaches can be used to design chloroplast transit peptides having CTP activity. Provided herein are recombinant polynucleotides encoding CTPs with sequences based on the alignment of various known monocot CTP sequences and the most frequent amino acids at each position operably linked to a heterologous polynucleotide encoding a polypeptide of interest. FIG. 2 provides the alignment of the various monocot CTP sequences used to determine the most frequent amino acids. The various CTPs were aligned based on the structural framework of the different domains as described elsewhere herein and a consensus CTP sequence is provided.

In one embodiment, a CTP is provided comprising the following CTP consensus sequence:

```
                                                      (SEQ ID NO: 11)
MXXXXVXXAAAXXXXSXPXXRXXXGXXXXXXXXXXXXXXXXXXAAXX

RXXXX::
``` or an active variant thereof, where the X indicates any amino acid.

Based on the consensus sequence, various CTPs can be constructed such that the resulting CTP has CTP activity. In some cases, a dominant amino acid residue may not be apparent. In these cases, one of the more frequent amino acid residues can be chosen to be incorporated into the sequence. It is recognized that many CTP sequences can be provided from the consensus sequence disclosed herein.

In one non-limiting embodiment, a CTP is provided having the following sequence:

```
                                                       (SEQ ID NO: 6)
MALASVMAAAAASVVSFPAGRGSGGSSVLRSRALSLAGSRRSAAAVRR

LAL:: (msCTP6)
``` or an active variant or fragment thereof. In another non-limiting embodiment, a CTP sequence is provided having the following sequence:

```
                                                       (SEQ ID NO: 7)
MAVATVLAAAALAAVSPPGLRSSLGFPVVRRSLPSAARGGSPAATRRCR

AA:: (msCTP7)
``` or an active variant or fragment thereof.

c. Other Components of the CTPs Provided Herein

It is recognized that the various CTPs disclosed herein can be modified to improve and/or alter the translocation of the polypeptide of interest into the chloroplast. For example, the CTP can contain additional regions that alter or improve the interactions with cytosolic factors that facilitate the passage of precursors from the ribosomes to the chloroplast surface. See, for example, Hiltbrunner et al. (2001) *Journal of Cell Biology* 154:309-316, Jackson-Constan et al. (2001) *Biochimica et Biophysica Acta* 1541:102-113, both of which are herein incorporated by reference. Other regions can be employed to increase the efficiency of chloroplast import. See, for example, May et al. (2000) *Plant Cell* 12:53-64, Qbadou et al. (2006) *EMBO Journal* 25:1837-1837 and Sohrt et al. (2000) *Journal of Cell Biology* 148:1213-1221, herein incorporated by reference. Such regions may be native (derived from a region of the same chloroplast targeted polypeptide as the CTP) or heterologous to the operably linked CTP provided herein.

The various CTPs disclosed herein can further comprise additional sequences which modulate the final location of the polypeptide of interest in the chloroplast. For example, the various CTPs disclosed herein could further comprise a thylakoid lumen targeting domain. Proteins to be targeted to the thylakoid lumen bear an additional cleavable targeting signal, which like the transit peptide, is removed once translocation is complete. The luminal targeting peptides are extremely similar to the signal peptides that mediate inner membrane transport in bacteria. See, for example, Keegstra et al. (1999) *Plant Cell* 11:557-570, Jarvis (2004) *Current Biology* 14: R1064-R1077, Gutensohn et al. (2006) *Journal of Plant Physiology* 163:333-347, and Jarvis (2008) *New Phytologist* 179:257-285, all of which are incorporated by reference in their entirety, which discuss the various sorting pathways in a chloroplast. Such regions which modulate the location of the polypeptide of interest in a chloroplast may be native (derived from a region of the same chloroplast targeted polypeptide as the CTP) or heterologous to the operably linked CTP provided herein.

The term "chloroplast transit peptide cleavage site" refers to a site between two amino acids in a chloroplast-targeting sequence at which the chloroplast processing protease acts. CTPs target the desired protein to the chloroplast and can facilitate the protein's translocation into the organelle. This is accompanied by the cleavage of the transit peptide from the mature polypeptide or protein at the appropriate transit peptide cleavage site by a chloroplast processing protease. Accordingly, a CTP can further comprise a suitable cleavage site for the correct processing of the pre-protein to the mature polypeptide contained within the chloroplast. In one non-limiting example, the CTP cleavage site is within the N-terminus of the IP2-127 protein between amino acid 15 and 16 in SEQ ID NO: 12, when msCTP4 was used in combination with IP2-127. As discussed above, the sequences beyond the cleaved fragments may be important for localization/transport efficiency and be employed with any of the CTPs disclosed herein.

d. Polynucleotide and Polypeptide Fragments and Variants of CTPs

Fragments and variants of the CTP-sequences (i.e. SEQ ID NOS: 1-7 and 13-23) are also encompassed herein. By "fragment" is intended a portion of the polynucleotide or a portion of the amino acid sequence and hence protein encoded thereby. Fragments of a polynucleotide may encode protein fragments that retain CTP activity when reconstituted in a CTP and are thus capable of facilitating the translocation of a polypeptide of interest into the chloroplast of a plant. Alternatively, fragments of a polynucleotide that are useful as a hybridization probe generally do not encode fragment proteins retaining biological activity. Thus, fragments of a nucleotide sequence may range from at least about 10, 20, 30, 40, 50, 60, 70, 80 nucleotides or up to the full length CTP.

A fragment of a polynucleotide that encodes a biologically active portion of a CTP-polypeptide will encode at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 contiguous amino acids, or up to the total number of amino acids present in any one of SEQ ID NOS: 1, 2, 3, 4, 5, 6, 7, 13, 14, 15, 16, 17, 18, 19, 20, 21, 22, 23 or of the various chimeric CTPs disclosed herein. Fragments of a CTP-encoding sequence that are useful as hybridization probes or PCR primers generally need not encode a biologically active portion of a CTP.

"Variant" CTP is intended to mean a protein derived from the CTP (i.e. SEQ ID NOS: 1-7 and 13-23) by deletion (i.e., truncation at the 5' and/or 3' end) and/or a deletion or addition of one or more amino acids at one or more internal sites in the CTP and/or substitution of one or more amino acids at one or more sites in the CTP, and/or substitution of one or more of the N-terminal, central, or C-terminal domains of the CTP and/or substitution of a portion of one or more of the N-terminal, central, or C-terminal domains of the CTP. Variant proteins encompassed are biologically active, that is they continue to possess the desired biological activity of the CTP, that is, have CTP activity when reconstituted in a CTP. Such variants may result from, for example, genetic polymorphism or from human manipulation.

For polynucleotides encoding a CTP, a variant comprises a polynucleotide having a deletion (i.e., truncations) at the 5' and/or 3' end and/or a deletion and/or addition of one or more nucleotides at one or more internal sites within the polynucleotide and/or a substitution of one or more nucleotides at one or more sites in the polynucleotide and/or substitution of one or more of the N-terminal, central, or C-terminal domains of the polynucleotide encoding the CTP and/or substitution of a portion of one or more of the N-terminal, central, or C-terminal domains of the polynucleotide encoding the CTP. Variant polynucleotides also include synthetically derived polynucleotides, such as those generated, for example, by using site-directed mutagenesis or gene synthesis but which still encode a CTP.

Biologically active variants of a CTP provided herein (and the polynucleotide encoding the same) will have at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more sequence identity to the polypeptide of any one of SEQ ID NO: 1, 2, 3, 4, 5, 6, 7, 13, 14, 15, 16, 17, 18, 19, 20, 21, 22, 23 or to any N-terminal domain or portion thereof, any central domain or portion thereof or any C-terminal domain or portion thereof from any one of SEQ ID NOS: 1-7, 13-43 or any of the other CTPs disclosed herein.

The CTP-sequences and the active variants and fragments thereof may be altered in various ways including amino acid substitutions, deletions, truncations, and insertions. Methods for such manipulations are generally known in the art. For example, amino acid sequence variants and fragments of the CTPs can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Obviously, the mutations that will be made in the DNA encoding the variant must not place the sequence out of reading frame and optimally will not create complementary regions that could produce secondary mRNA structure. See, EP Patent Application Publication No. 75,444.

Variant polynucleotides and proteins also encompass sequences and proteins derived from a mutagenic and recombinogenic procedure such as DNA shuffling. With such a procedure, one or more different CTP-sequences can be manipulated to create a new CTP possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the CTP sequences disclosed herein and other known CTPs to obtain a new polynucleotide coding for a polypeptide with an improved property of interest, such as an improved efficiency of transport to the chloroplast. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

e. Sequence Comparisons

The following terms are used to describe the sequence relationships between two or more polynucleotides or polypeptides: (a) "reference sequence", (b) "comparison window", (c) "sequence identity", and, (d) "percent sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence or protein sequence.

(b) As used herein, "comparison window" makes reference to a contiguous and specified segment of a polypeptide sequence, wherein the polypeptide sequence in the comparison window may comprise additions or deletions (i.e., gaps) compared to the reference sequence (which does not comprise additions or deletions) for optimal alignment of the two polypeptides. Generally, the comparison window is at least 5, 10, 15, or 20 contiguous amino acids in length, or it can be 30, 40, 50, 100, or longer. Those of skill in the art understand that to avoid a high similarity to a reference sequence due to inclusion of gaps in the polypeptide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local-alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. BLASTP protein searches can be performed using default parameters. See, blast.ncbi.nlm.nih.gov/Blast.cgi.

To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTP for proteins) can be used. See www.ncbi.nlm.nih.gov. Alignment may also be performed manually by inspection.

In one embodiment, sequence identity/similarity values provided herein refer to the value obtained using GAP Version 10 using the following parameters: % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity). When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percent sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percent sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percent sequence identity.

(e) Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acids substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Natl. Acad. Sci. USA 89:10915-10919. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (http://www.ncbi.nlm.nih.gov). Optimal alignments, including multiple alignments, can be prepared using, e.g., PSI-BLAST, available through http://www.ncbi.nlm.nih.gov and described by Altschul et al. (1997) *Nucleic Acids Res.* 25:3389-3402.

As used herein, similarity score and bit score is determined employing the BLAST alignment used the BLOSUM62 substitution matrix, a gap existence penalty of 11, and a gap extension penalty of 1. For the same pair of sequences, if there is a numerical difference between the scores obtained when using one or the other sequence as query sequences, a greater value of similarity score is selected.

C. Polynucleotides/Polypeptides of Interest

Any heterologous polynucleotide of interest (i.e., the "polypeptide of interest") may be used with the CTP-encoding sequences disclosed herein (i.e. the various chimeric CTPs disclosed herein and/or SEQ ID NOS: 1, 2, 3, 4, 5, 6, 7 or active variants or fragments thereof). It is recognized that any polypeptides of interest can be operably linked to the CTP-encoding sequences provided herein and expressed in a plant.

Such polynucleotides/polypeptides of interest include, but are not limited to, herbicide-tolerance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g., the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference.

Polynucleotides that improve crop yield include dwarfing genes, such as Rht1 and Rht2 (Peng et al. (1999) *Nature* 400:256-261), and those that increase plant growth, such as ammonium-inducible glutamate dehydrogenase. Polynucleotides that improve desirability of crops include, for example, those which allow plants to have a reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference.

These polynucleotide sequences of interest may encode proteins involved in providing disease or pest resistance. By "disease resistance" or "pest resistance" is intended that the plants avoid the harmful symptoms that are the outcome of the plant-pathogen interactions. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products.

In some embodiments, a CTP provided herein is operably linked to a heterologous polypeptide of interest comprising an insecticidal protein and expression of the polypeptide controls a pest (i.e. insecticidal activity). As used herein, by "controlling a pest" or "controls a pest" is intended any affect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack, or deterring the pests from eating the plant.

"Pest" includes, but is not limited to, insects, fungi, bacteria, viruses, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera. Viruses include but are not limited to tobacco or cucumber mosaic virus, ringspot virus, necrosis virus, maize dwarf mosaic virus, etc. Nematodes include but are not limited to parasitic nematodes such as root knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include but are not limited to *Pratylenchus* spp. Fungal pests include those that cause leaf, yellow, stripe and stem rusts.

In other embodiments, a polypeptide of interest comprises a *Bacillus thuringiensis* polypeptide having insecticidal activity (i.e. controls a pest). Some examples of *Bacillus thuringiensis* toxic proteins include the Cry proteins. Other *Bacillus thuringiensis* toxic proteins are described in U.S.

Pat. Nos. 5,366,892; 5,747,450; 5,737,514; 5,723,756; 5,593,881; and Geiser et al. (1986) *Gene* 48:109, herein incorporated by reference. In a specific embodiment, the *Bacillus thuringiensis* polypeptide is IP2-127 (SEQ ID NO: 12) or an active variant or fragment thereof. IP2-127 is a Cry2 protein of *Bacillus thuringiensis* with insecticidal activity. The IP2-127 protein may be modified to comprise, for example, a short linker sequence or a reporter gene in order to allow detection of the protein. An Example of a modified IP2-127 protein sequence is set forth in SEQ ID NO: 8 or an active variant or fragment thereof and is encoded by the polynucleotide sequence set forth in SEQ ID NO:9 or an active variant or fragment thereof and comprises an IP2-127-AcGFP fusion protein.

It is recognized that any polypeptide of interest may be modified to comprise, for example, a short linker sequence or a reporter gene in order to allow detection of the protein in the chloroplast.

Active variants or fragments of polynucleotides/polypeptides of interest (i.e. SEQ ID NO:12) are also provided. Such active variants can comprise at least 65%, 70%, 75%, 80%, 85%, 90%, 91%, 92%, 93%, 94%, 95%, 96%, 97%, 98%, 99% or more sequence identity to the native polynucleotide/polypeptide of interest, wherein the active variants retain biological activity and are functional in chloroplasts. Active fragments can comprise nucleic acid/amino acid sequences having at least 20, 25, 30, 35, 40, 50, 60, 70, 80, 100, 150, or more consecutive nucleic acids/amino acids of the native polynucleotide/polypeptide of interest, where the active fragments retain biological activity and are functional in chloroplasts. As used herein, a "native" polynucleotide or polypeptide comprises a naturally occurring nucleotide sequence or amino acid sequence, respectively. Methods to determine sequence identity/sequence similarity are described in detail elsewhere herein.

D. Plants

Compositions comprising a cell, a transgenic plant cell, a transgenic plant, transgenic plant parts and seeds, plant explants and grain having the recombinant polynucleotide encoding a CTP operably linked to a heterologous polynucleotide encoding a polypeptide of interest are further provided. In one embodiment, a cell, a plant cell, a plant, plant parts and seeds, plant explants and grain comprise at least one polynucleotide encoding a CTP provided herein (i.e. The various chimeric CTPs disclosed herein and/or SEQ ID NOS: 1, 2, 3, 4, 5, 6, 7 or active variants or fragments thereof) operably linked to a polypeptide of interest. The CTP may comprise a chimeric CTP, a chimeric CTP comprising chimeric domains, or a CTP comprising a consensus sequence as described in detail elsewhere herein. In some cases, the polynucleotide encoding the polypeptide of interest can comprise an insecticidal protein that controls a pest, a *Bacillus thuringiensis* protein having insecticidal activity, or an IP2-127 protein (i.e. SEQ ID NO:12) or active variant or fragment thereof.

As used herein, the term plant includes whole plants, plant organs, plant tissues, seeds and plant cells and progeny of the same, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included, provided that these parts comprise the introduced recombinant polynucleotides.

A transformed plant or transformed plant cell provided herein is one in which genetic alteration, such as transformation, has been affected as to a gene of interest, or is a plant or plant cell which is descended from a plant or cell so altered and which comprises the alteration. A "transgene" is a gene that has been introduced into the genome by a transformation procedure. Accordingly, a "transgenic plant" is a plant that contains a transgene, whether the transgene was introduced into that particular plant by transformation or by breeding; thus, descendants of an originally-transformed plant are encompassed by the definition. A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell. A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which does not express the CTP operably linked to a polypeptide of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the recombinant polynucleotide; or (e) the subject plant or plant cell itself, under conditions in which the recombinant polynucleotide is not expressed.

Plant cells that have been transformed to have a recombinant polynucleotide encoding a CTP operably linked to a polypeptide of interest provided herein can be grown into whole plants. The regeneration, development, and cultivation of plants from single plant protoplast transformants or from various transformed explants is well known in the art. See, for example, McCormick et al. (1986) *Plant Cell Reports* 5:81-84; Weissbach and Weissbach, In: Methods for Plant Molecular Biology, (Eds.), Academic Press, Inc. San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. Two or more generations may be grown to ensure that expression of the desired phenotypic characteristic is stably maintained and inherited and then seeds harvested to ensure expression of the desired phenotypic characteristic has been achieved. In this manner, the compositions presented herein provide transformed seed (also referred to as "transgenic seed") having a polynucleotide provided herein, for example, a recombinant polynucleotide encoding a CTP operably linked to a polypeptide of interest, stably incorporated into their genome.

The recombinant polynucleotides disclosed herein may be used for transformation of any plant species, including, but not limited to, monocots (e.g., maize, sugarcane, wheat, rice, barley, sorghum, or rye) and dicots (e.g., soybean, *Brassica*, sunflower, cotton, or alfalfa). Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include, but not limited to, tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include, but not limited to, azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*), and Poplar and Eucalyptus. In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

In some embodiments, the recombinant polynucleotides comprising the CTP-encoding sequence operably linked to the polynucleotide encoding the polypeptide of interest are engineered into a molecular stack. Thus, the various plants, plant cells and seeds disclosed herein can further comprise one or more traits of interest, and in more specific embodiments, the plant, plant part or plant cell is stacked with any combination of polynucleotide sequences of interest in order to create plants with a desired combination of traits. As used herein, the term "stacked" includes having the multiple traits present in the same plant.

These stacked combinations can be created by any method including, but not limited to, breeding plants by any conventional methodology, or genetic transformation. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

Depending on the polypeptide of interest, the transgenic plants, plant cells or seeds expressing a recombinant polynucleotide provided herein may have a change in phenotype, including but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified carbohydrate content and/or composition, a modified ability to utilize, partition and/or store nitrogen, and the like.

E. Polynucleotide Constructs

Also provided are isolated or recombinant polynucleotides and nucleic acid constructs that encode the CTPs disclosed herein (i.e. the various chimeric CTPs disclosed herein and/or SEQ ID NOS: 1, 2, 3, 4, 5, 6, 7 or active variants or fragments thereof) operably linked to a polynucleotide encoding a polypeptide of interest. As used herein, "encodes" or "encoding" refers to a DNA sequence which can be processed to generate an RNA and/or polypeptide.

The terms "polynucleotide," "polynucleotide sequence," "nucleic acid sequence," and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides provided herein also encompass all forms of sequences including, but not limited to, single-stranded forms, double-stranded forms, hairpins, stem-and-loop structures, and the like.

The compositions provided herein can comprise an isolated or substantially purified polynucleotide. An "isolated" or "purified" polynucleotide is substantially or essentially free from components that normally accompany or interact with the polynucleotide as found in its naturally occurring environment. Thus, an isolated or purified polynucleotide is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived.

Further provided are recombinant polynucleotides comprising the CTP sequences and polynucleotide sequences encoding the polypeptides of interest. The terms "recombinant polynucleotide" and "recombinant DNA construct" are used interchangeably herein. A recombinant construct comprises an artificial or heterologous combination of nucleic acid sequences, e.g., regulatory and coding sequences that are not found together in nature. For example, a recombinant polynucleotide can comprise a chimeric CTP operably linked to a heterologous polynucleotide encoding a polypeptide of interest. In other embodiments, a recombinant construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others.

The recombinant polynucleotides disclosed herein can be provided in expression cassettes for expression in a plant or other organism or cell type of interest. The cassette can include 5' and 3' regulatory sequences operably linked to the recombinant polynucleotide or active variant or fragment thereof. "Operably linked" is intended to mean a functional linkage between two or more elements. For example, an operable linkage between a polynucleotide of interest and a regulatory sequence (i.e., a promoter) is a functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the recombinant polynucleotide or active variant or fragment thereof to be under the transcriptional regulation of the regulatory regions. The expression cassette may additionally contain selectable marker genes.

The expression cassette can include in the 5'-3' direction of transcription, a transcriptional and translational initiation region (i.e., a promoter), a CTP-encoding sequence or active variant or fragment thereof operably linked to a polynucleotide encoding a polypeptide of interest and a transcriptional and translational termination region (i.e., termination region) functional in plants. The regulatory regions (i.e., promoters, transcriptional regulatory regions, and translational termination regions) and/or the CTP-encoding sequence and/or the polynucleotide encoding the polypeptide of interest may be native/analogous to the host cell or to each other. Alternatively, the regulatory regions and/or the CTP-encoding sequence and/or the polynucleotide encoding the polypeptide of interest may be heterologous to the host cell or to each other. In specific embodiments, the CTP-encoding sequence is operably linked to the 5' end of the polynucleotide of interest, such that, in the resulting recombinant polypeptide, the CTP is operably linked to the N-terminal region of the polypeptide of interest.

As used herein, "heterologous" in reference to a sequence is a sequence that originates from a foreign species, for example, from a different CTP, or, if from the same species, is substantially modified from its native form in composition and/or genomic locus by deliberate human intervention. For example, a heterologous domain is intended at least one of the CTP domains is not from the same CTP, but could be from a different CTP of the same plant species or a different plant species. In another example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The termination region may be native with the transcriptional initiation region, may be native with the operably linked polynucleotide sequence of interest, may be native with the plant host, or may be derived from another source (i.e., foreign or heterologous) to the promoter, the CTP, the polynucleotide sequence of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

In preparing the expression cassette, the various DNA fragments may be manipulated, so as to provide for the DNA sequences in the proper orientation. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385. See also, Della-Cioppa et al. (1987) *Plant Physiol.* 84:965-968.

A number of promoters can be used to express the recombinant polynucleotides provided herein. The promoters can be selected based on the desired outcome. It is recognized that different applications can be enhanced by the use of different promoters in the expression constructs to modulate the timing, location and/or level of expression of the recombinant polynucleotide. Such expression constructs may also contain, if desired, a promoter regulatory region (e.g. one conferring inducible, constitutive, environmentally- or developmentally regulated, or cell- or tissue-specific/selective expression), a transcription initiation start site, a ribosome binding site, an RNA processing signal, a transcription termination site, and/or a polyadenylation signal. including the native promoter of the polynucleotide sequence of interest.

In some embodiments, an expression construct provided herein can be combined with constitutive, tissue-preferred, or other promoters for expression in plants. Examples of constitutive promoters include, for example, the cauliflower mosaic virus (CaMV) 35S transcription initiation region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683, 439), the Nos promoter, the pEmu promoter, the rubisco promoter, the GRP1-8 promoter and other transcription initiation regions from various plant genes known to those of skill. If low level expression is desired, weak promoter(s) may be used. Weak constitutive promoters include, for example, the core promoter of the Rsyn7 promoter (WO 99/43838 and U.S. Pat. No. 6,072,050), the core 35S CaMV promoter, and the like. Other constitutive promoters include, for example, U.S. Pat. Nos. 5,608,149; 5,608,144; 5,604,121; 5,569,597; 5,466,785; 5,399,680; 5,268,463; and 5,608,142. See also, U.S. Pat. No. 6,177,611, herein incorporated by reference.

Examples of inducible promoters are the Adh1 promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the ERE promoter which is estrogen induced, and the Axig1 promoter which is auxin induced and tapetum specific but also active in callus (PCT US01/22169).

Examples of promoters under developmental control include promoters that initiate transcription preferentially in certain tissues, such as leaves, roots, fruit, seeds, or flowers. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A. et al. (1986) *Plant Sci.* 47:95-102; Reina, M. et al. *Nucl. Acids Res.* 18(21):6426; and Kloesgen, R. B. et al. (1986) *Mol. Gen. Genet.* 203:237-244. Promoters that express in the embryo, pericarp, and endosperm are disclosed in U.S. Pat. No. 6,225, 529 and PCT publication WO 00/12733. The disclosures for each of these are incorporated herein by reference in their entirety.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression or a recombinant polynucleotide within a particular plant tissue. Tissue-preferred promoters are known in the art. See, for example, Yamamoto et al. (1997) *Plant J* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590. In addition, the promoters of cab and rubisco can also be used. See, for example, Simpson et al. (1958) *EMBO J* 4:2723-2729 and Timko et al. (1988) *Nature* 318:57-58.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, sulfonylureas, dicamba, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Bairn et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference. The above list of selectable marker genes is not meant to be limiting. Any selectable marker gene can be employed herein, including for example, Ac-GFP as described in Examples 2 and 3.

II. Methods of Introducing

The methods provided herein comprise introducing into a cell, plant cell, plant or seed a recombinant polynucleotide or nucleic acid construct encoding a CTP provided herein (i.e. Any of the chimeric CTPs provided herein and/or SEQ ID NOS: 1, 2, 3, 4, 5, 6, 7 or active variants or fragments thereof) operably linked to a heterologous polynucleotide encoding a polypeptide of interest.

In some embodiments, the CTP introduced in the recombinant polynucleotide can be a chimeric CTP, a chimeric CTP comprising at least one chimeric domain, or a CTP comprising a consensus sequence as described in detail elsewhere herein. The CTP may be linked to any polypeptide of interest. For example, the polypeptide of interest can comprise an insecticidal protein whose expression controls a pest, a *Bacillus thuringiensis* polypeptide having insecticidal activity, or an IP2-127 polypeptide (i.e. SEQ ID NO:12 or an active variant or fragment thereof).

The methods provided herein do not depend on a particular method for introducing a sequence into the host cell, only that the polynucleotide gains access to the interior of a least one cell of the host. Methods for introducing polynucleotides into host cells (i.e. plants) are known in the art and include, but are not limited to, stable transformation methods, transient transformation methods, and virus-mediated methods.

The terms "introducing" and "introduced" are intended to mean providing a nucleic acid (e.g., recombinant polynucleotide) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant polynucleotide) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Stable transformation" is intended to mean that the nucleotide construct introduced into a host (i.e., a plant) integrates into the genome of the plant and is capable of being inherited by the progeny thereof. "Transient transformation" is intended to mean that a polynucleotide is introduced into the host (i.e., a plant) and expressed temporally.

Transformation protocols as well as protocols for introducing polynucleotide sequences into plants may vary depending on the type of plant or plant cell, i.e., monocot or dicot, targeted for transformation. Suitable methods of introducing polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the recombinant polynucleotides disclosed herein can be provided to a plant using a variety of transient transformation methods. Such transient transformation methods include, but are not limited to, the introduction of the recombinant polynucleotide or variants thereof directly into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotides can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use of particles coated with polyethylimine (PEI; Sigma #P3143).

In other embodiments, recombinant polynucleotides disclosed herein may be introduced into plants by contacting plants with a virus or viral nucleic acids. Generally, such methods involve incorporating a nucleotide construct provided herein within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the recombinant polynucleotides provided herein can be contained in a transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The recombinant polynucleotide is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, transformed seed (also referred to as "transgenic seed") having a recombinant polynucleotide disclosed herein, for example, an expression cassette provided herein, stably incorporated into their genome is provided.

III. Methods of Use

Provided herein is a method of targeting a polypeptide of interest to a chloroplast comprising expressing a recombinant polynucleotide encoding a CTP provided herein (i.e. Any of the chimeric CTPs provided herein and/or SEQ ID NOS: 1, 2, 3, 4, 5, 6, 7 or active variants or fragments thereof) operably linked to a heterologous polynucleotide encoding a polypeptide of interest in a cell, plant cell, plant, plant part or seed.

The methods further provide a CTP comprising a chimeric CTP, a chimeric CTP comprising at least one chimeric domain, or a CTP comprising a consensus sequence as described in detail elsewhere herein. The recombinant polynucleotide provided in the methods can comprise a CTP provided herein linked to any polypeptide of interest. For example, the polypeptide of interest can comprise an insecticidal protein whose expression controls a pest, a *Bacillus thuringiensis* polypeptide having insecticidal activity, or an IP2-127 polypeptide (i.e. SEQ ID NO:12 or an active variant or fragment thereof).

Methods of the present invention are directed to the proper expression, translocation, and processing of chloroplast-targeted sequences in plants and plant cells under the control of the CTP sequences disclosed herein. For the purposes of the present invention, a "processed" chloroplast targeted protein is one in which the CTP has been removed. At the time of translocation of a chloroplast targeted protein into the chloroplast of a plant cell, the CTP is removed from the targeted protein by cleavage at a particular "cleavage site" between the CTP and the mature protein. The cleavage site can be determined experimentally, or may be predicted based on sequence structure (e.g., by alignment of the unprocessed protein with chloroplast targeted proteins in which the cleavage site is known, by analyzing the sequence for the presence of characteristic CTP domains, and the like) or by using one or more algorithms for cleavage site prediction (e.g., SignalP or PSORT).

Depending on the polypeptide of interest targeted to the chloroplast, the transgenic plants may have a change in phenotype, including, but not limited to, an altered pathogen or insect defense mechanism, an increased resistance to one or more herbicides, an increased ability to withstand stressful environmental conditions, a modified ability to produce starch, a modified level of starch production, a modified oil content and/or composition, a modified ability to utilize, partition and/or store nitrogen, and the like. These results can be achieved through the expression and targeting of a polypeptide of interest to chloroplasts in plants, wherein the polypeptide of interest functions in the chloroplast. The CTP sequences provided herein are useful for targeting native sequences as well as heterologous (non-native) sequences in plants.

Non-limiting examples of methods and compositions disclosed herein are as follows:

1. A recombinant polynucleotide encoding a chloroplast transit peptide (CTP) operably linked to a heterologous polynucleotide encoding a polypeptide of interest, wherein the CTP comprises
   a) an amino acid sequence comprising the amino acids of SEQ ID NOS: 6 or 7;
   b) an amino acid sequence having at least 85% sequence identity to SEQ ID NOS: 6 or 7, wherein said amino acid sequence has CTP activity; or,
   c) an amino acid sequence having at least 17 consecutive amino acids of SEQ ID NOS: 6 or 7, wherein said amino acid sequence has CTP activity.

2. A recombinant polynucleotide encoding a chimeric chloroplast transit peptide (CTP) operably linked to a heterologous polynucleotide encoding a polypeptide of interest, wherein said chimeric CTP comprises an N-terminal domain, a central domain, and a C-terminal domain, or variant thereof, wherein at least one of said N-terminal domain, said central domain, said C-terminal domain or variant thereof is heterologous to at least one of said domains.

3. The recombinant polynucleotide of embodiment 2, wherein said N-terminal domain, said central domain or said C-terminal domain is from a CTP from *Oryza sativa* 1-deoxy-D xyulose-5-Phosphate Synthase, *Oryza sativa*-Superoxide dismutase, *Oryza sativa*-soluble starch synthase, *Oryza sativa*-NADP-dependent Malic acid enzyme, *Oryza sativa*-Phospho-2-dehydro-3-deoxyheptonate Aldolase 2, *Oryza sativa*-L-Ascorbate peroxidase 5, *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type or active variants thereof.

4. The recombinant polynucleotide of embodiment 2 or 3, wherein said N-terminal domain is from a CTP from *Oryza sativa* 1-deoxy-D xyulose-5-Phosphate Synthase, *Oryza sativa*-NADP-dependent Malic acid enzyme, *Zea Mays*-Malate dehydrogenase or active variants thereof.

5. The recombinant polynucleotide of embodiment 2 or 3, wherein said central domain is from a CTP from *Oryza sativa*-Superoxide dismutase, *Oryza sativa*-Phospho-2-dehydro-3-deoxyheptonate Aldolase 2, *Oryza sativa*-L-Ascorbate peroxidase 5, *Zea Mays* ssRUBISCO or active variants thereof.

6. The recombinant polynucleotide of embodiment 2 or 3, wherein said C-terminal domain is from a CTP from *Oryza sativa*-soluble starch synthase, *Oryza sativa*-Superoxide dismutase, *Oryza sativa*-Phosphoglucan water dikinase, *Zea Mays* Thioredoxin M-type, *Zea Mays*-beta-glucosidase or active variants thereof.

7. The recombinant polynucleotide of embodiment 2 or 3, wherein said N-terminal domain is from the *Oryza sativa* 1-deoxy-D xyulose-5-Phosphate Synthase CTP or an active variant thereof, said central domain is from the *Zea Mays* ssRUBISCO CTP or an active variant thereof and said C-terminal domain is from the *Zea Mays*-beta-glucosidase CTP or an active variant thereof.

8. The recombinant polynucleotide of embodiment 2 or 3, wherein said N-terminal domain is from the *Zea Mays*-Malate dehydrogenase CTP or an active variant thereof, said central domain is from the *Oryza sativa*-Superoxide dismutase CTP or an active variant or thereof and said C-terminal domain is from the *Oryza sativa*-soluble starch synthase CTP or an active variant thereof.

9. The recombinant polynucleotide of embodiment 2 or 3, wherein said N-terminal domain is from the *Oryza sativa*-NADP-dependent Malic acid enzyme CTP or an active variant thereof, said central domain is from the *Oryza sativa*-Phospho-2-dehydro-3-deoxyheptonate Aldolase 2 CTP or an active variant thereof and said C-terminal domain is from the *Zea Mays* Thioredoxin M-type CTP or an active variant thereof.

10. The recombinant polynucleotide of embodiment 2, wherein at least one of said N-terminal domain, said central domain, or said C-terminal domain comprises a chimeric domain.

11. The recombinant polynucleotide of embodiment 10, wherein at least one portion of said chimeric N-terminal domain is from the N-terminal domain of the *Oryza sativa*-NADP-dependent Malic CTP, *Zea Mays*-Malate dehydrogenase CTP or active variants thereof.

12. The recombinant polynucleotide of embodiment 10, wherein at least one portion of said chimeric central domain is from the central domain of the *Oryza sativa*-L-Ascorbate peroxidase 5 CTP, *Zea Mays* ssRUBISCO CTP or active variants thereof.

13. The recombinant polynucleotide of embodiment 10, wherein at least one portion of said chimeric C-terminal domain is from the C-terminal domain of the *Oryza sativa*-soluble starch synthase CTP, *Zea Mays* Thioredoxin M-type CTP, *Oryza sativa*-Superoxide dismutase CTP, *Oryza sativa*-Phosphoglucan water dikinase CTP or active variants thereof.

14. The recombinant polynucleotide of embodiment 10, wherein said chimeric CTP comprises
   a) a chimeric N-terminal domain, wherein said chimeric N-terminal domain comprises a portion of the N-terminal domain from the *Zea Mays*-Malate dehydrogenase CTP fused in frame to a portion of the N-terminal domain of the *Oryza sativa*-NADP-dependent Malic acid enzyme CTP;
   b) a central domain, wherein said central domain is from the *Zea Mays* ssRUBISCO CTP; and,
   c) a chimeric C-terminal domain, wherein said chimeric C-terminal domain comprises a portion of the C-terminal domain from the *Oryza sativa*-soluble starch synthase CTP fused in frame to a portion of the C-terminal domain from the *Zea Mays* Thioredoxin M-type CTP;
   wherein said chimeric CTP has CTP activity.

15. The recombinant polynucleotide of embodiment 10, wherein said chimeric CTP comprises
   a) a chimeric N-terminal domain, wherein said chimeric N-terminal domain comprises a portion of the N-terminal domain from the *Zea Mays*-Malate dehydrogenase CTP fused in frame to a portion of the N-terminal domain of the *Oryza sativa*-NADP-dependent Malic acid enzyme CTP;
   b) a chimeric central domain, wherein said chimeric central domain comprises a portion of the central domain from the *Oryza sativa*-L-Ascorbate peroxidase 5 CTP fused in frame to a portion of the central domain of the *Zea Mays* ssRUBISCO CTP; and,
   c) a chimeric C-terminal domain, wherein said chimeric C-terminal domain comprises a portion of the C-terminal domain from the *Oryza sativa*-Superoxide dismutase CTP fused in frame to a portion of the C-terminal domain of the *Oryza sativa*-Phosphoglucan water dikinase CTP;
   wherein said chimeric CTP has CTP activity.

16. The recombinant polynucleotide of embodiment 3, wherein the chimeric CTP comprises a) an amino acid sequence comprising the amino acids of SEQ ID NOS: 1, 2 or 3;
b) an amino acid sequence having at least 85% sequence identity to SEQ ID NOS: 1, 2 or 3, wherein said amino acid sequence has CTP activity; or
c) an amino acid sequence having at least 17 consecutive amino acids of SEQ ID NOS: 1, 2 or 3, wherein said amino acid sequence has CTP activity.

17. The recombinant polynucleotide of embodiment 14, wherein the chimeric CTP comprises
a) an amino acid sequence comprising the amino acids of SEQ ID NO: 4;
b) an amino acid sequence having at least 85% sequence identity to SEQ ID NO: 4, wherein said amino acid sequence has CTP activity; or
c) an amino acid sequence having at least 17 consecutive amino acids of SEQ ID NO: 4, wherein said amino acid sequence has CTP activity.

18. The recombinant polynucleotide of embodiment 15, wherein the chimeric CTP comprises
a) an amino acid sequence comprising the amino acids of SEQ ID NO: 5;
b) an amino acid sequence having at least 85% sequence identity to SEQ ID NO: 5, wherein said amino acid sequence has CTP activity; or
c) an amino acid sequence having at least 17 consecutive amino acids of SEQ ID NO: 5, wherein said amino acid sequence has CTP activity.

19. The recombinant polynucleotide of any one of embodiments 1-18, wherein said polypeptide of interest comprises a *Bacillus thuringiensis* polypeptide having insecticidal activity.

20. The recombinant polynucleotide of embodiment 19, wherein said *Bacillus thuringiensis* polypeptide having insecticidal activity comprises an IP2-127 polypeptide.

21. A nucleic acid construct comprising the recombinant polynucleotide of any one of embodiments 1-20.

22. The nucleic acid construct of embodiment 21, further comprising a promoter operably linked to said recombinant polynucleotide.

23. A cell comprising at least one recombinant polynucleotide of any of embodiments 1-20 or the nucleic acid construct of any one of embodiments 21 or 22.

24. The cell of embodiment 23, wherein said cell is a plant cell.

25. The cell of embodiment 24, wherein said polynucleotide or nucleic acid construct is stably incorporated into the genome of said plant cell.

26. The cell of any one of embodiments 24 or 25, wherein said plant cell is from a monocot.

27. The cell of embodiment 26, wherein said monocot is maize, wheat, rice, barley, sorghum, sugarcane or rye.

28. The cell of any one of embodiments 24 or 25, wherein said plant cell is from a dicot.

29. The cell of embodiment 28, wherein the dicot is soybean, *Brassica*, sunflower, cotton or alfalfa.

30. A plant comprising at least one plant cell of any one of embodiments 24-29.

31. A plant explant comprising at least one plant cell of any one of embodiments 24-29.

32. A transgenic seed produced by the plant of embodiment 30, wherein said seed comprises said recombinant polynucleotide.

33. A recombinant polypeptide encoded by the polynucleotide of any one of embodiments 1-20.

34. A method of targeting a polypeptide of interest to a chloroplast comprising expressing the recombinant polynucleotide of any one of embodiments 1-20 or the nucleic acid construct of embodiment 21 or 22 in a plant cell.

35. A method of targeting a polypeptide of interest to a chloroplast comprising introducing the recombinant polynucleotide of any one of embodiments 1-20 or the nucleic acid construct of embodiment 21 or 22 in a plant cell and expressing said recombinant polynucleotide in the plant cell.

36. The method of embodiment 34 or 35, wherein said method further comprises regenerating a transgenic plant from said plant cell.

37. The method of any one of embodiments 34-36, wherein said plant cell is from a monocot.

38. The method of embodiment 37, wherein said monocot is selected from the group consisting of maize, wheat, rice, barley, sorghum, sugarcane or rye.

39. The method of any one of embodiments 34-36, wherein said plant cell is from a dicot.

40. The method of embodiment 39, wherein said dicot is selected from the group consisting of soybean, *Brassica*, sunflower, cotton or alfalfa.

41. The method of any one of embodiments 35-40, wherein said polypeptide of interest comprises an insecticidal protein and expression of said polypeptide controls a pest.

42. The method of embodiment 41, wherein said polypeptide of interest comprises a *Bacillus thuringiensis* polypeptide having insecticidal activity.

43. The method of embodiment 42, wherein said *Bacillus thuringiensis* polypeptide having insecticidal activity comprises an IP2-127 polypeptide.

EXPERIMENTAL

The following examples are offered to illustrate, but not to limit, the claimed invention. It is understood that the examples and embodiments described herein are for illustrative purposes only, and persons skilled in the art will recognize various reagents or parameters that can be altered without departing from the spirit of the invention or the scope of the appended claims.

Example 1

Development of Novel Chloroplast Targeting Peptides (CTPs) for Maize

Nuclear encoded plant proteins that are translated in the cytosol are targeted to the chloroplast using an N-terminal transit peptide. CTPs are both necessary and sufficient for correct chloroplast targeting and these signal peptides are of variable length and sequence. Although there is no consensus peptide sequence CTPs do share a similar structural framework consisting of an uncharged N-terminus, a central region lacking acidic residues but enriched in hydroxylated amino acids, and a basic arginine-rich amphipathic C-terminus.

Two approaches were employed to develop these targeting peptides based on the alignment of a set of known or predicted chloroplast transit peptides from monocotyledonous species (see FIG. 1). The first approach utilized was to generate chimeric CTPs based on the predicted boundaries of the different CTP domains described above. The new CTPs can be derived from 3 or more different plant CTP sequences that when combined together collectively reconstitute a CTP. A set of 5 different chimeric CTPs were generated based on the CTP alignment found in FIG. 1. msCTP1 (SEQ ID NO: 1: MALTTFSISRGGFVGALQGLKSTASLP-NNESFSRHHLPSSSPQSSKRRCNLSFT TR) was generated from the combination of domains in sequential order from Oryza sativa (Os) 1-deoxy-D xylulose-5-Phosphate Synthase CTP (aa 1-17), Zea mays (Zm) ssRUBISCO CTP (aa 18-27) and Zm-beta-glucosidase CTP (aa 28-56). msCTP2 (SEQ ID NO: 2: MGLSTVYSPAGPRLVPA-PASLFQSPSSGCHSCWGPGPGGGRRLPS PRRRPIT-GTRS) was generated from the combination of domains in sequential order from Zm-Malate dehydrogenase (NADP) CTP (aa 1-17), Os-Superoxide dismutase (SOD) CTP (aa 18-27) and Os-Soluble starch synthase CTP (aa 28-52). msCTP3 (SEQ ID NO: 3: MLSARAAATAAAAAASP-PQPRLAATFLVLPSKRALAPLLSVGRVA TRRPRH-VCQ) was generated from the combination of the following domains in sequential order from Os-NADP-dependent Malic acid enzyme CTP (aa 1-17), Os-Phospho-2-dehydro-3-deoxyheptonate (PHD) Aldolase 2 CTP (aa 18-27), and Zm Thioredoxin M-type (TRX) CTP (aa 28-54). msCTP4 (SEQ ID NO: 4: MGLSTVYSPAAAAAASP-PQPRSTASLPGCHSCWGPGPLLSVGRVATRRPR HVCQ) was generated with the combination of domains in sequential order from Zm-Malate dehydrogenase (NADP) CTP (aa 1-9), Os-NADP-dependent Malic acid enzyme CTP CTP (aa 10-21), Zm-ssRUBSICO CTP (aa 22-27), Os-Soluble starch synthase CTP (aa 28-37), and Zm-Thioredoxin (TRX) CTP (aa 38-54). The design of msCTP4 incorporated sequences derived from 2 separate CTPs for the first and third domains. msCTP5 (SEQ ID NO: 5: MGLSTVYS-PAAAAAASPPSLRSTASLPARPFHSLRLAAG RRG-FACRGRSAAS) was generated with the combination of domains in sequential order from Zm-Malate dehydrogenase (NADP) CTP (aa 1-9), Os-NADP-dependent Malic acid enzyme CTP CTP (aa 10-17), Os-L-Ascorbate peroxidase 5(OsAPx05) (aa 18-21); Zm-ssRUBSICO CTP (aa 22-27), Os-Superoxide dismutase (OsSOD) CTP (aa 28-39), and Os-Phosphoglucan water dikinase (OsPGDK) CTP (aa 40-52).

The second approach used the most frequent amino acid at each position based on the alignment of the different CTPs that were of a similar size (50-60 aa). In some cases where no dominant amino acid residue was apparent one of the more frequent amino acid residues was chosen to be incorporated into the sequence. Two CTPs were developed using this strategy. msCTP6 (SEQ ID NO: 6: MALASVMAAAAASVVS-FPAGRGSGG SSVLRSRALSLAGSRRSAAAVRRLAL) and msCTP7 (SEQ ID NO: 7: MAVATVLAAAALAAVSP-PGLRSSLGFPVVRRSLPSAARGGSPAATRRCRAA).

A comparison of the amino acid identity levels for the different CTPs developed using this strategy is found in Table 1. The homology between all the CTPs ranged from 16-64%.

Example 2

Construction of Vectors for Testing the Ability of the Novel CTPs to Target an Insecticidal Toxin to the Chloroplast A transient expression vector was generated to evaluate the ability of the novel CTPs to target an insecticidal toxin, IP2-127, to the maize chloroplast. This vector contained a fusion gene with IP2-127 at the N-terminus and AcGFP at the C terminus separated by a short linker sequence (SEQ ID NO: 8: ATGGGCAACAGCGTGCTCAACAGCG-GACGCACCACCATCTGCGACGCCTACA ACGTGGC-CGCGCACGACCCGTTCAGCTTCCAGCA-CAAGAGCCTCGACACCGT GCAGCGCGAGTGGACCGAGTGGAAGAA-GAACAACCACAGCCTCTACCTCGA CCCGATCGTGGGCACCGTGGCCAGCTTC-CTCCTCAAGAAGGTGGGCAGCCTC GTGGGCAAGCGCATCCTCAGCGAGCT-GCGCAACCTCATCTTCCCGAGCGGCA GCACCAAC-CTCATGCAGGACATCCTCCGCGAGAC-CGAGCAGTTCCTCAACCA GCGCCTCGACACCGACACCCTCGC-CAGGGTGAACCCGAGCTGACCGGCCTC CAGGC-CAACGTGGAGGAGTTCAACCGCCAGGTG-GACAACTTCCTCAACCCGA ACCGCAACGCCGTGCCGCTCAGCATCAC-CAGCAGCGTGAACACCATGCAGCA GCTCTTCCT-CAACCGCCTCCCGCAGTTCCAGATG-CAGGGCTACCAGCTCCTGC TCCTGCCGCTCTTCGCCCAGGCCGC-CAACCTCCACCTCAGCTTCATCCGCGAC GTGATC-CTCAACGCCGACGAGTGGGGCAT-CAGCGCCGCCACCCTCCGCACCT ACCGCGACTACCTCAAGAACTACAC-CCGCGACTACAGCAACTACTGCATCAA CACCTAC-CAGAGCGCCTTCAAGGGCCTCAACAC-CCGCCTCCACGGCACCCTC GAGTTCCGCACCTACATGTTCCT-CAACGTCTTCGAGTACGTGAGCATCTGGAG CCTCT-TCAAGTACCAGAGCCTCCTCGTGAG-CAGCGGCGCCAACCTCTACGCC AGCGGCAGCGGCCCGCAGCAGACCCA-GAGCTTCACCAGCCAGGACTGGCCG TTCCTCTA-CAGCCTCTTCCAGGTGAACAGCAAC-TACGTGCTCAACGGCTTCAG CGGCGCCAGGCTCAGCAACACCTTC-CCGAACATCGGCGGCCTCCCGGGCAGC ACCAC-CACCCACGCCCTCCTCGCGGCCAGGGT-GAACTACAGCGGCGGCATCA GCAGCGGCGACATCGGCGCCAGCCCGT-

TABLE 1

| msCTP identity table. |
| --- |

| | msCTP1 | msCTP3 | msCTP4 | msCTP5 | msCTP2 | msCTP6 | msCTP7 |
| --- | --- | --- | --- | --- | --- | --- | --- |
| msCTP1 | | 16 | 26 | 28 | 16 | 20 | 22 |
| msCTP3 | | | 64 | 38 | 21 | 38 | 36 |
| msCTP4 | | | | 59 | 46 | 31 | 36 |
| msCTP5 | | | | | 33 | 34 | 44 |
| msCTP2 | | | | | | 35 | 26 |
| msCTP6 | | | | | | | 47 |
| msCTP7 | | | | | | | |

TCAACCAGAACTTCAACTGCAGCAC CTTCCTC-CCGCCGCTCCTCACCCCGTTCGTGCG-CAGCTGGCTCGATAGCGGCA GCGACCGCGAGGGCGTGGCCACCGTGAC-CAACTGGCAGACCGAGAGCTTCG AGACCA-CACTCGGGCTCAGGAGCGGCGCCTTCAC-CGCCCGCGGCAACAGCAA CTACTTCCCGGACTACTTCATCCGGAA-CATCTCCGGCGTTCCGTTGGTGGTCC GTAACGAG-GATCTCAGGAGGCCGCTGCACTACAAC-GAGATCCGCAACATCGC TTCGCCCAGCGGGACCCCAGGTGGAG-CACGGGCCTACATGGTGTCCGTGCAC AACCGGAA-GAACAACATCCACGCGGTCCAT-GAGAACGGCAGCATGATCCAC CTGGCTCCTAACGACTACACGGGGTTCA-CAATCTCTCCGATCCATGCTACTCA AGTCAACAAC-CAGACCAGGACGTTCATCTCGGAGAAGT-TCGGCAACCAGGG AGACTCCTTGAGGTTCGAGCAGAACAA-CACAACTGCCCGCTACACCCTTCGG GGCAACGG-GAACAGCTACAACCTCTACCTGCGCGT-CAGCTCCATCGGCAACT CGACGATCAGGGTCACGATCAACG-GAAGGGTCTACACTGCGACCAACGTGA ACACGA-CAACTAACAACGACGGCGTCAACGA-CAACGGCGCTAGGTTCTCCGA CATCAACATCGGGAACGTTGTG-GCAAGCTCCAACTCGGATGTCCCTCTTGAC ATCAACGTCACCTTCAACTCTGGAACG-CAGTTCGATCTGATGAACACAATGCT GGTGCCAAC-TAACATCAGCCCTCTGTACGGTGGAG-GCGGCAGCGGTGGCGGA GGCTCCGGAGGCGGTGGCTCCATGGT-GAGCAAGGGCGCCGAGCTGTTCACCG GCATCGT-GCCCATCCTGATCGAGCTGAATGGCGAT-GTGAATGGCCACAAGTT CAGCGTGAGCGGCGAGGGCGAGGGCGAT-GCCACCTACGGCAAGCTGACCCT GAAGTTCATCTG-CACCACCGGCAAGCTGCCTGTGCCCTG-GCCCACCCTGGTG ACCACCCTGAGCTACGGCGTGCAGTGCT-TCTCACGCTACCCCGATCACATGA AGCAGCAC-GACTTCTTCAAGAGCGCCATGCCT-GAGGGCTACATCCAGGAGCG CACCATCTTCTTCGAGGATGACGGCAAC-TACAAGTCGCGCGCCGAGGTGAAG TTCGAGGGC-GATACCCTGGTGAATCGCATCGAGCT-GACCGGCACCGATTTCA AGGAGGATGGCAACATCCTGGGCAATAA-GATGGAGTACAACTACAACGCCC ACAATGTGTA-CATCATGACCGACAAGGCCAAGAATG-GCATCAAGGTGAACTT CAAGATCCGCCACAACATCGAGGATG-GCAGCGTGCAGCTGGCCGACCACTAC CAGCA-GAATACCCCCATCGGCGATGGCCCTGT-GCTGCTGCCCGATAACCACT ACCTGTCCACCCAGAGCGCCCTGTC-CAAGGACCCCAACGAGAAGCGCGATCA CATGATC-TACTTCGGCTTCGTGACCGCCGCCGC-CATCACCCACGGCATGGATG AGCTGTACAAGTGA) which encoded a IP2-127-AcGFP fusion protein (SEQ ID NO: 9: MGNSVLNSGRTTICDAYNVAAHDPFS-FQHKSLDTVQREWTEWKKNNHSL YLDPIVGTVAS-FLLKKVGSLVGKRILSELRNLIFPSGST-NLMQDILRETEQFLNQR LDTDTLARVNAELTGLQANVEEFNRQVD-NFLNPNRNAVPLSITSSVNTMQQLFL NRLPQFQM-QGYQLLLLPLFAQAANLHLSFIRDVIL-NADEWGISAATLRTYRDYLK NYTRDYSNYCINTYQSAFKGLNTRLH-GTLEFRTYMFLNVFEYVSIWSLFKYQSLL VSSGANL-YASGSGPQQTQSFTSQDWPFLYSLFQVN-SNYVLNGFSGARLSNTFPNI GGLPGSTTHALLAARVNYSGGISSGDI-GASPFNQNFNCSTFLPPLLTPFVRSWLD SGSDREG-VATVTNWQTESFETTLGLRSGAFTARGN-SNYFPDYFIRNISGVPLVVR NEDLRRPLHYNEIRNIASPSGTPGGA-RAYMVSVHNRKNNIHAVHENGSMIHLAP NDYTGFT-ISPIHATQVNNQTRTFISEKFGNQGDSL-RFEQNNTTARYTLRGNGNSY NLYLRVSSIGNSTIRVTINGRVYTAT-NVNTTINNDGVNDNGARFSDINIGNVVAS SNSDV-PLDINVTFNSGTQFDLMNTMLVPTNIS-PLYGGGGSGGGGSGGGGSMVSK GAELFTGIVPILIELNGDVNGHKFSVS-GEGEGDATYGKLTLKFICTTGKLPVPWPT LVTTL-SYGVQCFSRYPDHMKQHDFFKSAMP-EGYIQERTIFFEDDGNYKSRAEVK FEGDTLVNRIELTGTDFKEDGNILGNKM-EYNYNAHNVYIMTDKAKNGIKVNFKI RHNIEDGS-VQLADHYQQNTPIGDGPVLLPDNHYL-STQSALSKDPNEKRDHMIYF GFVTAAAITHGMDELYK) consisting of IP2-127 from amino acid 1-634, a short 15 aa linker from amino acid 635-649, and AcGFP from amino acid 650-888. The IP2-127::AcGFP fusion gene is under control of the strong constitutive maize Ubiquitin 1 promoter-5'UTR-intron1 regulatory element in vector pSK-UB1-IP2-127::AcGFP with a pinII transcriptional terminator sequence. The vector contains unique BamHI and KpnI restriction enzyme sites immediately upstream of the IP2-127 translational start codon to facilitate an in frame insertion of different CTP sequences at the N-terminus of the fusion.

The different novel monocot CTPs were synthesized by DNA2.0 (Menlo park, CA). Each CTP was subcloned into pSK-UB1-IP2-127::AcGFP using the unique BamHI and KpnI restriction sites. The base vector, pSK-UBI-IP2-127::AcGFP, was used as a control for non-CTP targeted IP2-127::AcGFP. A vector containing IP2-127::AcGFP fused to a previously characterized CTP derived by gene shuffling (6H1-CTP) (SEQ ID NO: 10: MAATTLTSALPGAFSSSQRPSAPFNLQR-SPRVLRRFNRKTGRQ PRGLVRAAKAQ) was used as a positive control for chloroplast targeting in transient expression assays.

Example 3

Transient Expression Assays to Identify Novel CTPs Effective at Targeting IP2-127::AcGFP to the Maize Chloroplast Maize seedlings were generated in soilless artificial condition by embedding kernels between two sheets of seed germination paper in a roll and its bottom portion was submerged in 0.1 mg/ml sucrose solution. Leaf segments were detached from seedlings at 15 days post-planting immediately before ballistic co-bombardment with colloidal gold particles transformation. The lower epidermis of the leaf segments were excised and overlaid on top of filter papers in 100 mm Petri dishes.

The samples were co-bombarded with DNAs from both a DS-RED plasmid vector and individual CTP testing vectors using the PDS-1000 He biolistic particle delivery system (Bio-Rad, Hercules Calif.). Gold particles (1.0 µm in diameter; Bio-Rad) were coated with plasmid DNAs following the procedure described by Sanford et al. (1993) with modifications. Briefly, 50 µl of freshly prepared gold particles in water (20 mg/ml), and 20 µl of DNA mixture, which contain 10 µg of equimolar quantities of the DS Red helper plasmid and CTP testing plasmids, were combined and 50 µl of a 2.5 M CaCl$_2$ solution and 20 µl of freshly prepared 0.1 M spermidine (Sigma-Aldrich, St Louis Mo.) were slowly added with gentle vortexing. The mixture was incubated at room temperature for 5 min and pelleted at 13,000 g in a microcentrifuge for 5 sec. The supernatant was carefully removed and the pellet was resuspended in 85 µl of 100% ethanol. While gently vortexing, a 6 µl aliquot of suspension was drawn and dispensed onto the center of a macrocarrier membrane. The membrane was allowed to air dry completely for 2-5 min and used immediately. Leaf segments were bombarded at a distance of 9 cm from an 1100-psi rupture disk. Two replicate shots were performed from each coating preparation. After bombardment, the leaf samples were incubated in a moist chamber at 28 degree Celsius.

Initial examination was conducted at approximately 24 h post-bombardment with a Lumar fluorescence stereomicroscope (Carl Zeiss Inc., Thornwood N.Y.) equipped with both a green-emitting (Zeiss Set 10) and red-emitting (Zeiss Set 43 HE) filter set to image the AcGFP and the DsRed2, respectively. The leaf segments containing AcGFP-positive cells identified in the stereomicroscope were placed in a 0.01% Tween 20 solution and a vacuum was applied for about 10 min to remove internal air and to wet the leaf surface. The leaves were placed into coverglass chambers (Nalge Nunc International, Rochester N.Y.) in the same solution, sealed with an additional coverglass and examined in the LSM510 (Carl Zeiss). AcGFP fluorescence was captured using a 488 nm argon laser for excitation and a 500-550 nm band pass emission filter. DsRed fluorescence was imaged using a 561 nm diode laser for excitation and a 575-615 nm band pass emission filter. Chlorophyll fluorescence was captured by combining 561 nm excitation and a 650-710 nm band pass emission filter.

DsRed expression was used to assess the overall transformation rate and was very useful for identifying transformed cells in the confocal microscope. Although epidermal cells were transformed with the highest frequency by the bombardment procedure, mesophyll cells were used to assess plastid targeting. Plastid targeting was confirmed by co-localizing the AcGFP signal with chlorophyll fluorescence. Plastid targeting was quantified with the confocal microscope by counting the number of mesophyll cells showing plastid-targeted AcGFP as a percentage of the total number of transformed cells (i.e., those exhibiting DsRed fluorescence).

The results of this analysis are outlined in Table 2. No colocalization of IP2-127::AcGFP with the chloroplast was observed in the non-targeted control where AcGFP fluorescence was limited exclusively to the cytosolic compartment. The majority of AcGFP derived fluorescence from the positive control, 6H1-CTP-IP2-127::AcGFP, was found to colocalize to chloroplasts and was scored at the highest level of +++. CTPs, msCTP1 and msCTP4, showed equivalent levels of chloroplast colocalization of IP2-127::AcGFP as observed with 6H1CTP. msCTP2 and msCTP6 directed IP2-127::AcGFP to the chloroplast although there was equal signal between chloroplast targeted and cytosolic localized fluorescence observed. This suggested that these two CTPs were not as efficient as msCTP1 or msCTP4 in chloroplast targeting. msCTP5 directed more cytosolic localization of IP2-127::AcGFP than chloroplast colocalization but detectable levels of chloroplast colocalization was observed. msCTP7 failed to direct any IP2-127::AcGFP to the chloroplast and was similar to the non-targeted control where IP2-127::AcGFP was cytosolic.

TABLE 2

Effectiveness of chloroplast targeting of novel CTPs based on colocalization of AcGFP fluorescence with maize chloroplasts in transient expression assays.

| Construct | Colocalization with chloroplasts |
|---|---|
| IP2-127::AcGFP (non-targeted control) | − |
| 6H1CTP-IP2-127::AcGFP (targeted control) | +++ |
| msCTP1-IP2-127::AcGFP | +++ |
| msCTP2-IP2-127::AcGFP | ++ |
| msCTP3-IP2-127::AcGFP | − |
| msCTP4-IP2-127::AcGFP | +++ |
| msCTP5-IP2-127::AcGFP | + |
| msCTP6-IP2-127::AcGFP | ++ |
| msCTP7-IP2-127::AcGFP | − |

+++ IP2-127::AcGFP mostly chloroplast localized
++ equal IP2-127::GFP detected in chloroplast and cytosol.
+ some IP2-127::AcGFP in chloroplast but mostly in cytosol
− IP2-127::GFP entirely in cytosol Example 4

Transgenic Plant Evaluation of Novel CTPs

The effect of chloroplast targeting was extended from transient expression assays to stable transgenic events expressing IP2-127 with different msCTPs. Chloroplast targeting of IP2-127 generally results in higher accumulation of IP2-127 in plants than would be observed when non-targeted. This difference in accumulation may be related to improved stability of IP2-127 in the chloroplast and/or phytotoxicity issues associated with high levels of accumulation of IP2-127 in the cytosol during the transformation process. Transformation vectors were generated using IP2-127 and a subset of the msCTPs-mCTP1, mCTP2, msCTP4, msCTP5, msCTP6—that were selected to represent the different qualitative results from the transient assays. Emphasis was put on those msCTPs that demonstrated some level of chloroplast colocalization in the transient experiments. The transformation vectors were generated by using a base vector containing the IP2-127 gene with unique BamHI and KpnI restriction enzyme sites directly upstream of the translation start codon (ATG) of IP2-127. Subcloning each of the msCTPs into the BamHI and KpnI sites created an N-terminal fusion with the msCTP protein sequence and the IP2-127 protein sequence. Non-targeted or msCTP targeted versions of the genes were placed under control of the maize Ubiquitin 1 promoter-5'UTR-Ubiquitin intron1 and terminated with the pinII terminator sequence from Potato creating the msCTP test cassette. The msCTP test cassettes were introduced into a binary transformation vector using standard Gateway™ LR Clonase reactions that were facilitated by the presence of attL3 and attL4 recombination sites flanking the test cassette and attR3 and attL4 sites in the destination transformation vector. The final product of the LR reaction was a transformation binary vector containing the msCTP-IP2-127 test cassette upstream of a cassette containing the maize Ubiquitin1 promoter-5'UTR- Ubiquitin intron1 controlling expression of a PAT selectable marker gene with the 35S terminator sequence.

Transgenic events derived from this set of msCTP testing vectors were evaluated for expression of IP2-127 by ELISA. The results of the ELISA analysis are shown in Table 3. Accumulation of IP2-127 in the cytosol was 511 ppm. The addition of the 6H1-CTP to the N-terminus of IP2-127 improved accumulation ~2.5-fold to 1294 ppm demonstrating the effect of an effective CTP on IP21-27 accumulation in plants. Two CTPs, msCTP1 and msCTP4, improved IP2-127 accumulation ~7.7-fold and ~5-fold over the non-targeted version and 2-3-fold over the level of accumulation directed by 6H1-CTP. msCTP2 and msCTP6 showed comparable levels of accumulation as 6H1-CTP with both versions improving accumulation ~2.5-fold over non-targeted IP2-127. No significant improvement in IP2-127 accumulation was observed with msCTP5 as the levels of accumulation were only about ~1.5-fold improved over the negative control. Overall, accumulation of IP2-127 in transgenic plants correlated well with the results of colocalization of IP2-127::AcGFP observed in transient expression assays. The results demonstrated that this strategy of developing new synthetic CTPs was effective at providing novel chloroplast targeting peptides and that many of the msCTPs developed enhanced accumulation of IP2-127 in transgenic maize plants.

TABLE 3

Accumulation of IP2-127 in transgenic maize events.

| Construct ID | No of Events Tested | IP2-127 Expression (PPM) |
|---|---|---|
| UBI-IP2-127 | 25 | 511 |
| UBI-6H1-CTP-IP2-127 | 21 | 1294 |
| UBI-msCTP1-IP2-127 | 23 | 3931 |
| UBI-msCTP2-IP2-127 | 24 | 1408 |
| UBI-msCTP4-IP2-127 | 25 | 2548 |
| UBI-msCTP5-IP2-127 | 23 | 802 |
| UBI-msCTP6-IP2-127 | 25 | 1406 |

TABLE 4

Summary of CTP domains.

| CTP | N-terminal Domain | Central Domain | C-terminal Domain |
|---|---|---|---|
| msCTP1 | SEQ ID NO: 24 | SEQ ID NO: 25 | SEQ ID NO: 26 |
| msCTP2 | SEQ ID NO: 27 | SEQ ID NO: 28 | SEQ ID NO: 29 |
| msCTP3 | SEQ ID NO: 30 | SEQ ID NO: 31 | SEQ ID NO: 32 |
| msCTP4 | SEQ ID NO: 33/ SEQ ID NO: 34 | SEQ ID NO: 35 | SEQ ID NO: 36/ SEQ ID NO: 37 |
| msCTP5 | SEQ ID NO: 38/ SEQ ID NO: 39 | SEQ ID NO: 40/ SEQ ID NO: 41 | SEQ ID NO: 42/ SEQ ID NO: 43 |

TABLE 5

Summary of SEQ ID NOS

| SEQ ID NO | NA/AA | Description |
|---|---|---|
| 1 | AA | msCTP1 |
| 2 | AA | msCTP2 |
| 3 | AA | msCTP3 |
| 4 | AA | msCTP4 |
| 5 | AA | msCTP5 |
| 6 | AA | msCTP6 |
| 7 | AA | msCTP7 |
| 8 | NA | Nucleotide sequence of IP2-127-AcGFP fusion protein |
| 9 | AA | Amino acid sequence of IP2-127-AcGFP fusion protein |
| 10 | AA | 6H1-CTP (positive control CTP) |
| 11 | AA | CTP Consensus Sequence |
| 12 | AA | IP2-127 Amino Acid sequence |
| 13 | AA | OS-1-deoxy-D-xyulose-5-Phosphate Synthase CTP |
| 14 | AA | OS-Superoxide dismutase CTP |
| 15 | AA | OS-soluble starch synthase CTP |
| 16 | AA | OS-NADP dependent Malic acid enzyme CTP |
| 17 | AA | OS-Phospho-2-dehydro-3-deoxyheptonate Aldolase 2 CTP |
| 18 | AA | OS-L-Ascorbate Peroxidase 5 CTP |
| 19 | AA | OS-Phosphoglucan water dikinase |
| 20 | AA | ZM-ssRUBISCO CTP |
| 21 | AA | ZM-beta-glucosidase CTP |
| 22 | AA | ZM-Malate dehydrogenase CTP |
| 23 | AA | ZM-Thioredoxin M-type |
| 24 | AA | Amino acids 1-17 of OS-1-deoxy-D-xyulose-5-Phosphate Synthase CTP, N-terminal domain of CTP1 |
| 25 | AA | Amino acids 18-27 of ZM-ssRUBISCO CTP, Central domain of CTP1 |
| 26 | AA | Amino acids 28-56 of ZM-beta-glucosidase CTP, C-terminal domain of CTP1 |
| 27 | AA | Amino acids 1-17 of ZM-Malate dehydrogenase CTP, N-terminal domain of CTP2 |
| 28 | AA | Amino acids 18-27 of OS-Superoxide dismutase CTP, Central domain of CTP2 |
| 29 | AA | Amino acids 28-52 of OS-soluble starch synthase CTP, C-terminal domain of CTP2 |
| 30 | AA | Amino acids 1-17 of OS-NADP dependent Malic acid enzyme CTP, N-terminal domain of CTP3 |
| 31 | AA | Amino acids 18-27 of OS-Phospho-2-dehydro-3-deoxyheptonate Aldolase 2 CTP, Central domain of CTP3 |
| 32 | AA | Amino acids 28-54 of ZM-Thioredoxin M-type, C-terminal domain of CTP3 |

TABLE 5-continued

Summary of SEQ ID NOS

| SEQ ID NO | NA/AA | Description |
|---|---|---|
| 33 | AA | Amino acids 1-9 of ZM-Malate dehydrogenase CTP, portion of N-terminal domain of CTP4 |
| 34 | AA | Amino acids 10-21 of OS-NADP dependent Malic acid enzyme CTP, portion of N-terminal domain of CTP4 |
| 35 | AA | Amino acids 22-27 of ZM-ssRUBISCO CTP, Central domain of CTP4 |
| 36 | AA | Amino acids 28-37 of OS-soluble starch synthase CTP, portion of C-terminal domain of CTP4 |
| 37 | AA | Amino acids 38-54 of ZM-Thioredoxin M-type, portion of C-terminal domain of CTP4 |
| 38 | AA | Amino acids 1-9 of ZM-Malate dehydrogenase CTP, portion of N-terminal domain of CTP5 |
| 39 | AA | Amino acids 10-17 of OS-NADP dependent Malic acid enzyme CTP, portion of N-terminal domain of CTP5 |
| 40 | AA | Amino acids 18-21 of OS-L-Ascorbate Peroxidase 5 CTP, portion of central domain of CTP5 |
| 41 | AA | Amino acids 22-27 of ZM-ssRUBISCO CTP, portion of central domain of CTP5 |
| 42 | AA | Amino acids 28-39 of OS-Superoxide dismutase CTP, portion of C-terminal domain of CTP5 |
| 43 | AA | Amino acids 40-52 of OS-Phosphoglucan water dikinase, portion of C-terminal domain of CTP5 |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant polynucleotide encoding a chloroplast transit peptide (CTP) operably linked to a heterologous polynucleotide encoding a polypeptide of interest, wherein the CTP comprises
   a) an amino acid sequence comprising the amino acid sequence set forth in SEQ ID NOS: 6 or 7; or
   b) an amino acid sequence having at least 85% sequence identity to SEQ ID NOS: 6 or 7, wherein said amino acid sequence has CTP activity.

2. A recombinant polynucleotide encoding a chimeric CTP comprising
   a) an amino acid sequence comprising the amino acid sequence set forth in SEQ ID NOS: 1,2 or 3; or
   b) an amino acid sequence having at least 85% sequence identity to SEQ ID NOS: 1, 2 or 3, wherein said amino acid sequence has CTP activity.

3. A recombinant polynucleotide encoding a chimeric CTP comprising
   a) an amino acid sequence comprising the amino acid sequence set forth in SEQ ID NO: 4; or
   b) an amino acid sequence having at least 85% sequence identity to SEQ ID NO: 4, wherein said amino acid sequence has CTP activity.

4. A recombinant polynucleotide encoding a chimeric CTP comprising
   a) an amino acid sequence comprising the amino acid sequence set forth in SEQ ID NO: 5; or
   b) an amino acid sequence having at least 85% sequence identity to SEQ ID NO: 5, wherein said amino acid sequence has CTP activity.

5. The recombinant polynucleotide of claim 1, wherein said polypeptide of interest comprises a *Bacillus thuringiensis* polypeptide having insecticidal activity.

6. The recombinant polynucleotide of claim 5, wherein said *Bacillus thuringiensis* polypeptide having insecticidal activity comprises an IP2-127 polypeptide.

7. A nucleic acid construct comprising the recombinant polynucleotide of claim 1, 2, 3 or 4.

8. The nucleic acid construct of claim 7, further comprising a promoter operably linked to said recombinant polynucleotide.

9. A cell comprising at least one recombinant polynucleotide of any one of claim 1, 2, 3 or 4.

10. The cell of claim 9, wherein said cell is a plant cell.

11. The cell of claim 10, wherein said polynucleotide is stably incorporated into the genome of said plant cell.

12. The cell of claim 10, wherein said plant cell is from a monocot or dicot.

13. The cell of claim 12, wherein said monocot is maize, wheat, rice, barley, sorghum, sugarcane or rye, and wherein said dicot is soybean, *Brassica*, sunflower, cotton or alfalfa.

14. A plant comprising at least one plant cell of claim 10.

15. A plant explant comprising at least one plant cell of claim 10.

16. A transgenic seed produced by the plant of claim 14, wherein said seed comprises said recombinant polynucleotide.

17. A recombinant polypeptide encoded by the polynucleotide of claim 1, 2, 3 or 4.

18. A method of targeting a polypeptide of interest to a chloroplast comprising expressing the recombinant polynucleotide of claim 1, 2, 3 or 4 in a plant cell.

\* \* \* \* \*

```
                       SEQUENCE LISTING

<160> NUMBER OF SEQ ID NOS: 56

<210> SEQ ID NO 1
<211> LENGTH: 56
<212> TYPE: PRT
<213> ORGANISM: Artificial Sequence
<220> FEATURE:
<223> OTHER INFORMATION: synthetic construct; Chimeric CTP- msCTP1

<400> SEQUENCE: 1

Met Ala Leu Thr Thr Phe Ser Ile Ser Arg Gly Gly Phe Val Gly Ala
1               5                   10                  15

Leu Gln Gly Leu Lys Ser Thr Ala Ser Leu Pro Asn Asn Glu Ser Phe
            20                  25                  30

Ser Arg His His Leu Pro Ser Ser Ser Pro Gln Ser Ser Lys Arg Arg
        35                  40                  45

Cys Asn Leu Ser Phe Thr Thr Arg
    50                  55

<210> SEQ ID NO 2
<211> LENGTH: 56
<212> TYPE: PRT
<213> ORGANISM: Artificial Sequence
<220> FEATURE:
<223> OTHER INFORMATION: synthetic construct; Chimeric CTP- msCTP2

<400> SEQUENCE: 2

Met Gly Leu Ser Thr Val Tyr Ser Pro Ala Gly Pro Arg Leu Val Pro
1               5                   10                  15
```

```
Ala Pro Ala Ser Leu Phe Gln Ser Pro Ser Ser Gly Cys His Ser Cys
             20                  25                  30

Trp Gly Pro Gly Pro Gly Gly Arg Leu Pro Ser Pro Arg Arg
         35                  40                  45

Arg Pro Ile Thr Gly Thr Arg Ser
     50                  55

<210> SEQ ID NO 3
<211> LENGTH: 54
<212> TYPE: PRT
<213> ORGANISM: Artificial Sequence
<220> FEATURE:
<223> OTHER INFORMATION: synthetic construct; Chimeric CTP- msCTP3

<400> SEQUENCE: 3

Met Leu Ser Ala Arg Ala Ala Thr Ala Ala Ala Ala Ala Ala Ala Ser
1               5                   10                  15

Pro Pro Gln Pro Arg Leu Ala Ala Thr Phe Leu Val Leu Pro Ser Lys
             20                  25                  30

Arg Ala Leu Ala Pro Leu Leu Ser Val Gly Arg Val Ala Thr Arg Arg
         35                  40                  45

Pro Arg His Val Cys Gln
     50

<210> SEQ ID NO 4
<211> LENGTH: 54
<212> TYPE: PRT
<213> ORGANISM: Artificial Sequence
<220> FEATURE:
<223> OTHER INFORMATION: synthetic construct; Chimeric CTP- msCTP4

<400> SEQUENCE: 4

Met Gly Leu Ser Thr Val Tyr Ser Pro Ala Ala Ala Ala Ala Ala Ser
1               5                   10                  15

Pro Pro Gln Pro Arg Ser Thr Ala Ser Leu Pro Gly Cys His Ser Cys
             20                  25                  30

Trp Gly Pro Gly Pro Leu Leu Ser Val Gly Arg Val Ala Thr Arg Arg
         35                  40                  45

Pro Arg His Val Cys Gln
     50

<210> SEQ ID NO 5
<211> LENGTH: 52
<212> TYPE: PRT
<213> ORGANISM: Artificial Sequence
<220> FEATURE:
<223> OTHER INFORMATION: synthetic construct; Chimeric CTP- msCTP5

<400> SEQUENCE: 5

Met Gly Leu Ser Thr Val Tyr Ser Pro Ala Ala Ala Ala Ala Ala Ser
1               5                   10                  15

Pro Pro Ser Leu Arg Ser Thr Ala Ser Leu Pro Ala Arg Pro Phe His
             20                  25                  30

Ser Leu Arg Leu Ala Ala Gly Arg Arg Gly Phe Ala Cys Arg Gly Arg
         35                  40                  45

Ser Ala Ala Ser
     50

<210> SEQ ID NO 6
<211> LENGTH: 51
<212> TYPE: PRT
```

<213> ORGANISM: Artificial Sequence
<220> FEATURE:
<223> OTHER INFORMATION: synthetic construct; msCTP6- CTP derived from consensus sequence

<400> SEQUENCE: 6

```
Met Ala Leu Ala Ser Val Met Ala Ala Ala Ala Ser Val Val Ser
1               5                   10                  15

Phe Pro Ala Gly Arg Gly Ser Gly Gly Ser Ser Val Leu Arg Ser Arg
            20                  25                  30

Ala Leu Ser Leu Ala Gly Ser Arg Arg Ser Ala Ala Ala Val Arg Arg
        35                  40                  45

Leu Ala Leu
    50
```

<210> SEQ ID NO 7
<211> LENGTH: 51
<212> TYPE: PRT
<213> ORGANISM: Artificial Sequence
<220> FEATURE:
<223> OTHER INFORMATION: synthetic construct; msCTP7- CTP derived from consensus sequence

<400> SEQUENCE: 7

```
Met Ala Val Ala Thr Val Leu Ala Ala Ala Leu Ala Ala Val Ser
1               5                   10                  15

Pro Pro Gly Leu Arg Ser Ser Leu Gly Phe Pro Val Val Arg Arg Ser
            20                  25                  30

Leu Pro Ser Ala Ala Arg Gly Gly Ser Pro Ala Ala Thr Arg Arg Cys
        35                  40                  45

Arg Ala Ala
    50
```

<210> SEQ ID NO 8
<211> LENGTH: 2667
<212> TYPE: DNA
<213> ORGANISM: Artificial Sequence
<220> FEATURE:
<223> OTHER INFORMATION: synthetic construct; Nucleotide sequence of IP2-127-AcGFP fusion protein

<400> SEQUENCE: 8

```
atgggcaaca gcgtgctcaa cagcggacgc accaccatct cgacgcccta caacgtggcc      60
gcgcacgacc cgttcagctt ccagcacaag agcctcgaca ccgtgcagcg cgagtggacc     120
gagtggaaga gaacaaccca cagcctctac ctcgacccga tcgtgggcac cgtggcagcc    180
ttcctcctca agaaggtggg cagcctcgtg ggcaagcgca tcctcagcga gctgcgcaac    240
ctcatcttcc cgagcggcag caccaacctc atgcaggaca cctccgcga gaccgagcag    300 ttcctcaacc agcgcctcga caccgacacc ctcgccaggg tgaacgccga gctgaccggc    360
ctccaggcca acgtggagga gttcaaccgc caggtggaca cttcctcaa cccgaaccgc    420 aacgccgtgc cgctcagcat caccagcagc gtgaacacca tgcagcagct cttcctcaac    480
cgcctcccgc agttccagat gcagggctac cagctcctgc cctgccgct cttcgcccag    540 gccgccaacc tccacctcag cttcatccgc gacgtgatcc tcaacgccga cgagtggggc    600
atcagcgccg ccaccctccg cacctaccgc gactacctca gaactacac ccgcgactac    660 agcaactact gcatcaacac ctaccagagc gccttcaagg gctcaacac ccgcctccac    720 ggcaccctcg agttccgcac ctacatgttc ctcaacgtct cgagtacgt gagcatctgg    780
```

```
agcctcttca agtaccagag cctcctcgtg agcagcggcg ccaacctcta cgccagcggc    840
agcggcccgc agcagaccca gagcttcacc agccaggact ggccgttcct ctacagcctc    900
ttccaggtga acagcaacta cgtgctcaac ggcttcagcg cgccaggct cagcaacacc     960
ttcccgaaca tcggcggcct cccgggcagc accaccaccc acgccctcct cgcggccagg   1020
gtgaactaca gcggcggcat cagcagcggc gacatcggcg ccagcccgtt caaccagaac   1080
ttcaactgca gcaccttcct cccgccgctc ctcaccccgt tcgtgcgcag ctggctcgat   1140
agcggcagcg accgcgaggg cgtggccacc gtgaccaact ggcagaccga gagcttcgag   1200
accacactcg ggctcaggag cggcgccttc accgcccgcg caacagcaa ctacttcccg    1260
gactacttca tccggaacat ctccggcgtt ccgttggtgg tccgtaacga ggatctcagg   1320
aggccgctgc actacaacga gatcgcaac atcgcttcgc ccagcgggac cccaggtgga    1380
gcacgggcct acatggtgtc cgtgcacaac cggaagaaca catccacgc ggtccatgag    1440
aacggcagca tgatccacct ggctcctaac gactacacgg ggttcacaat ctctccgatc   1500
catgctactc aagtcaacaa ccagaccagg acgttcatct cggagaagtt cggcaaccag   1560
ggagactcct tgaggttcga gcagaacaac acaactgccc gctacaccct tcggggcaac   1620
gggaacagct acaacctcta cctgcgcgtc agctccatcg gcaactcgac gatcagggtc   1680
acgatcaacg gaagggtcta cactgcgacc aacgtgaaca cgacaactaa caacgacggc   1740
gtcaacgaca acggcgctag gttctccgac atcaacatcg gaacgttgt ggcaagctcc    1800
aactcggatg tccctcttga catcaacgtc accttcaact ctggaacgca gttcgatctg   1860
atgaacacaa tgctggtgcc aactaacatc agccctctgt acggtggagg cggcagcggt   1920
ggcggaggct ccggaggcgg tggctccatg gtgagcaagg gcgccgagct gttcaccggc   1980
atcgtgccca tcctgatcga gctgaatggc gatgtgaatg ccacaagtt cagcgtgagc    2040
ggcgagggcg agggcgatgc cacctacggc aagctgaccc tgaagttcat ctgcaccacc   2100
ggcaagctgc ctgtgccctg cccaccctg gtgaccaccc tgagctacgg cgtgcagtgc    2160
ttctcacgct accccgatca catgaagcag cacgacttct tcaagagcgc catgcctgag   2220
ggctacatcc aggagcgcac catcttcttc gaggatgacg gcaactacaa gtcgcgcgcc   2280
gaggtgaagt tcgagggcga taccctggtg aatcgcatcg agctgaccgg caccgatttc   2340
aaggaggatg gcaacatcct gggcaataag atggagtaca actacaacgc ccacaatgtg   2400
tacatcatga ccgacaaggc caagaatggc atcaaggtga acttcaagat ccgccacaac   2460
atcgaggatg gcagcgtgca gctggccgac cactaccagc agaataccc catcggcgat    2520
ggccctgtgc tgctgcccga taaccactac ctgtccaccc agagcgccct gtccaaggac   2580
cccaacgaga gcgcgatca catgatctac ttcggcttcg tgaccgccgc cgccatcacc    2640
cacggcatgg atgagctgta caagtga                                       2667
```

<210> SEQ ID NO 9
<211> LENGTH: 888
<212> TYPE: PRT
<213> ORGANISM: Artificial Sequence
<220> FEATURE:
<223> OTHER INFORMATION: synthetic construct; Amino acid sequence of
      IP2-127-AcGFP fusion protein

<400> SEQUENCE: 9

Met Gly Asn Ser Val Leu Asn Ser Gly Arg Thr Thr Ile Cys Asp Ala
1               5                   10                  15

Tyr Asn Val Ala Ala His Asp Pro Phe Ser Phe Gln His Lys Ser Leu

```
                    20                  25                  30
Asp Thr Val Gln Arg Glu Trp Thr Glu Trp Lys Lys Asn Asn His Ser
                35                  40                  45
Leu Tyr Leu Asp Pro Ile Val Gly Thr Val Ala Ser Phe Leu Leu Lys
            50                  55                  60
Lys Val Gly Ser Leu Val Gly Lys Arg Ile Leu Ser Glu Leu Arg Asn
65                  70                  75                  80
Leu Ile Phe Pro Ser Gly Ser Thr Asn Leu Met Gln Asp Ile Leu Arg
                85                  90                  95
Glu Thr Glu Gln Phe Leu Asn Gln Arg Leu Asp Thr Asp Thr Leu Ala
            100                 105                 110
Arg Val Asn Ala Glu Leu Thr Gly Leu Gln Ala Asn Val Glu Glu Phe
        115                 120                 125
Asn Arg Gln Val Asp Asn Phe Leu Asn Pro Asn Arg Asn Ala Val Pro
    130                 135                 140
Leu Ser Ile Thr Ser Ser Val Asn Thr Met Gln Gln Leu Phe Leu Asn
145                 150                 155                 160
Arg Leu Pro Gln Phe Gln Met Gln Gly Tyr Gln Leu Leu Leu Leu Pro
                165                 170                 175
Leu Phe Ala Gln Ala Ala Asn Leu His Leu Ser Phe Ile Arg Asp Val
            180                 185                 190
Ile Leu Asn Ala Asp Glu Trp Gly Ile Ser Ala Ala Thr Leu Arg Thr
        195                 200                 205
Tyr Arg Asp Tyr Leu Lys Asn Tyr Thr Arg Asp Tyr Ser Asn Tyr Cys
    210                 215                 220
Ile Asn Thr Tyr Gln Ser Ala Phe Lys Gly Leu Asn Thr Arg Leu His
225                 230                 235                 240
Gly Thr Leu Glu Phe Arg Thr Tyr Met Phe Leu Asn Val Phe Glu Tyr
                245                 250                 255
Val Ser Ile Trp Ser Leu Phe Lys Tyr Gln Ser Leu Leu Val Ser Ser
            260                 265                 270
Gly Ala Asn Leu Tyr Ala Ser Gly Ser Gly Pro Gln Gln Thr Gln Ser
        275                 280                 285
Phe Thr Ser Gln Asp Trp Pro Phe Leu Tyr Ser Leu Phe Gln Val Asn
    290                 295                 300
Ser Asn Tyr Val Leu Asn Gly Phe Ser Gly Ala Arg Leu Ser Asn Thr
305                 310                 315                 320
Phe Pro Asn Ile Gly Gly Leu Pro Gly Ser Thr Thr Thr His Ala Leu
                325                 330                 335
Leu Ala Ala Arg Val Asn Tyr Ser Gly Gly Ile Ser Ser Gly Asp Ile
            340                 345                 350
Gly Ala Ser Pro Phe Asn Gln Asn Phe Asn Cys Ser Thr Phe Leu Pro
        355                 360                 365
Pro Leu Leu Thr Pro Phe Val Arg Ser Trp Leu Asp Ser Gly Ser Asp
    370                 375                 380
Arg Glu Gly Val Ala Thr Val Thr Asn Trp Gln Thr Glu Ser Phe Glu
385                 390                 395                 400
Thr Thr Leu Gly Leu Arg Ser Gly Ala Phe Thr Ala Arg Gly Asn Ser
                405                 410                 415
Asn Tyr Phe Pro Asp Tyr Phe Ile Arg Asn Ile Ser Gly Val Pro Leu
            420                 425                 430
Val Val Arg Asn Glu Asp Leu Arg Arg Pro Leu His Tyr Asn Glu Ile
        435                 440                 445
```

```
Arg Asn Ile Ala Ser Pro Ser Gly Thr Pro Gly Ala Arg Ala Tyr
    450                 455                 460

Met Val Ser Val His Asn Arg Lys Asn Asn Ile His Ala Val His Glu
465                 470                 475                 480

Asn Gly Ser Met Ile His Leu Ala Pro Asn Asp Tyr Thr Gly Phe Thr
                485                 490                 495

Ile Ser Pro Ile His Ala Thr Gln Val Asn Asn Gln Thr Arg Thr Phe
            500                 505                 510

Ile Ser Glu Lys Phe Gly Asn Gln Gly Asp Ser Leu Arg Phe Glu Gln
        515                 520                 525

Asn Asn Thr Thr Ala Arg Tyr Thr Leu Arg Gly Asn Gly Asn Ser Tyr
    530                 535                 540

Asn Leu Tyr Leu Arg Val Ser Ser Ile Gly Asn Ser Thr Ile Arg Val
545                 550                 555                 560

Thr Ile Asn Gly Arg Val Tyr Thr Ala Thr Asn Val Asn Thr Thr Thr
                565                 570                 575

Asn Asn Asp Gly Val Asn Asp Asn Gly Ala Arg Phe Ser Asp Ile Asn
                580                 585                 590

Ile Gly Asn Val Val Ala Ser Ser Asn Ser Asp Val Pro Leu Asp Ile
        595                 600                 605

Asn Val Thr Phe Asn Ser Gly Thr Gln Phe Asp Leu Met Asn Thr Met
    610                 615                 620

Leu Val Pro Thr Asn Ile Ser Pro Leu Tyr Gly Gly Gly Ser Gly
625                 630                 635                 640

Gly Gly Gly Ser Gly Gly Gly Ser Met Val Ser Lys Gly Ala Glu
                645                 650                 655

Leu Phe Thr Gly Ile Val Pro Ile Leu Ile Glu Leu Asn Gly Asp Val
                660                 665                 670

Asn Gly His Lys Phe Ser Val Ser Gly Glu Gly Glu Gly Asp Ala Thr
                675                 680                 685

Tyr Gly Lys Leu Thr Leu Lys Phe Ile Cys Thr Thr Gly Lys Leu Pro
            690                 695                 700

Val Pro Trp Pro Thr Leu Val Thr Thr Leu Ser Tyr Gly Val Gln Cys
705                 710                 715                 720

Phe Ser Arg Tyr Pro Asp His Met Lys Gln His Asp Phe Phe Lys Ser
                725                 730                 735

Ala Met Pro Glu Gly Tyr Ile Gln Glu Arg Thr Ile Phe Phe Glu Asp
            740                 745                 750

Asp Gly Asn Tyr Lys Ser Arg Ala Glu Val Lys Phe Glu Gly Asp Thr
            755                 760                 765

Leu Val Asn Arg Ile Glu Leu Thr Gly Thr Asp Phe Lys Glu Asp Gly
    770                 775                 780

Asn Ile Leu Gly Asn Lys Met Glu Tyr Asn Tyr Asn Ala His Asn Val
785                 790                 795                 800

Tyr Ile Met Thr Asp Lys Ala Lys Asn Gly Ile Lys Val Asn Phe Lys
                805                 810                 815

Ile Arg His Asn Ile Glu Asp Gly Ser Val Gln Leu Ala Asp His Tyr
            820                 825                 830

Gln Gln Asn Thr Pro Ile Gly Asp Gly Pro Val Leu Leu Pro Asp Asn
        835                 840                 845

His Tyr Leu Ser Thr Gln Ser Ala Leu Ser Lys Asp Pro Asn Glu Lys
850                 855                 860
```

Arg Asp His Met Ile Tyr Phe Gly Phe Val Thr Ala Ala Ala Ile Thr
865                 870                 875                 880

His Gly Met Asp Glu Leu Tyr Lys
            885

<210> SEQ ID NO 10
<211> LENGTH: 54
<212> TYPE: PRT
<213> ORGANISM: Artificial Sequence
<220> FEATURE:
<223> OTHER INFORMATION: synthetic construct; 6H1-CTP (positive control
      CTP)- derived by gene shuffling

<400> SEQUENCE: 10

Met Ala Ala Thr Thr Leu Thr Ser Ala Leu Pro Gly Ala Phe Ser Ser
1               5                   10                  15

Ser Gln Arg Pro Ser Ala Pro Phe Asn Leu Gln Arg Ser Pro Arg Val
            20                  25                  30

Leu Arg Arg Phe Asn Arg Lys Thr Gly Arg Gln Pro Arg Gly Leu Val
        35                  40                  45

Arg Ala Ala Lys Ala Gln
    50

<210> SEQ ID NO 11
<211> LENGTH: 51
<212> TYPE: PRT
<213> ORGANISM: Artificial Sequence
<220> FEATURE:
<223> OTHER INFORMATION: synthetic construct; Consensus CTP Sequence
<220> FEATURE:
<221> NAME/KEY: misc_feature
<222> LOCATION: (2)..(5)
<223> OTHER INFORMATION: X can be any amino acid
<220> FEATURE:
<221> NAME/KEY: misc_feature
<222> LOCATION: (7)..(8)
<223> OTHER INFORMATION: X can be any amino acid
<220> FEATURE:
<221> NAME/KEY: misc_feature
<222> LOCATION: (12)..(15)
<223> OTHER INFORMATION: X can be any amino acid
<220> FEATURE:
<221> NAME/KEY: misc_feature
<222> LOCATION: (17)..(17)
<223> OTHER INFORMATION: X can be any amino acid
<220> FEATURE:
<221> NAME/KEY: misc_feature
<222> LOCATION: (19)..(20)
<223> OTHER INFORMATION: X can be any amino acid
<220> FEATURE:
<221> NAME/KEY: misc_feature
<222> LOCATION: (22)..(24)
<223> OTHER INFORMATION: X can be any amino acid
<220> FEATURE:
<221> NAME/KEY: misc_feature
<222> LOCATION: (26)..(42)
<223> OTHER INFORMATION: X can be any amino acid
<220> FEATURE:
<221> NAME/KEY: misc_feature
<222> LOCATION: (45)..(46)
<223> OTHER INFORMATION: X can be any amino acid
<220> FEATURE:
<221> NAME/KEY: misc_feature
<222> LOCATION: (48)..(51)
<223> OTHER INFORMATION: X can be any amino acid

<400> SEQUENCE: 11

Met Xaa Xaa Xaa Xaa Val Xaa Xaa Ala Ala Ala Xaa Xaa Xaa Xaa Ser
1               5                   10                  15

Xaa Pro Xaa Xaa Arg Xaa Xaa Xaa Gly Xaa Xaa Xaa Xaa Xaa Xaa Xaa

```
                    20                  25                  30
Xaa Xaa Xaa Xaa Xaa Xaa Xaa Xaa Xaa Ala Ala Xaa Xaa Arg Xaa
            35                  40                  45

Xaa Xaa Xaa
        50

<210> SEQ ID NO 12
<211> LENGTH: 634
<212> TYPE: PRT
<213> ORGANISM: Bacillus thuringiensis

<400> SEQUENCE: 12

Met Gly Asn Ser Val Leu Asn Ser Gly Arg Thr Thr Ile Cys Asp Ala
1               5                   10                  15

Tyr Asn Val Ala Ala His Asp Pro Phe Ser Phe Gln His Lys Ser Leu
            20                  25                  30

Asp Thr Val Gln Arg Glu Trp Thr Glu Trp Lys Lys Asn Asn His Ser
        35                  40                  45

Leu Tyr Leu Asp Pro Ile Val Gly Thr Val Ala Ser Phe Leu Leu Lys
    50                  55                  60

Lys Val Gly Ser Leu Val Gly Lys Arg Ile Leu Ser Glu Leu Arg Asn
65                  70                  75                  80

Leu Ile Phe Pro Ser Gly Ser Thr Asn Leu Met Gln Asp Ile Leu Arg
                85                  90                  95

Glu Thr Glu Gln Phe Leu Asn Gln Arg Leu Asp Thr Asp Thr Leu Ala
            100                 105                 110

Arg Val Asn Ala Glu Leu Thr Gly Leu Gln Ala Asn Val Glu Glu Phe
        115                 120                 125

Asn Arg Gln Val Asp Asn Phe Leu Asn Pro Asn Arg Asn Ala Val Pro
130                 135                 140

Leu Ser Ile Thr Ser Ser Val Asn Thr Met Gln Gln Leu Phe Leu Asn
145                 150                 155                 160

Arg Leu Pro Gln Phe Gln Met Gln Gly Tyr Gln Leu Leu Leu Leu Pro
                165                 170                 175

Leu Phe Ala Gln Ala Ala Asn Leu His Leu Ser Phe Ile Arg Asp Val
            180                 185                 190

Ile Leu Asn Ala Asp Glu Trp Gly Ile Ser Ala Ala Thr Leu Arg Thr
        195                 200                 205

Tyr Arg Asp Tyr Leu Lys Asn Tyr Thr Arg Asp Tyr Ser Asn Tyr Cys
    210                 215                 220

Ile Asn Thr Tyr Gln Ser Ala Phe Lys Gly Leu Asn Thr Arg Leu His
225                 230                 235                 240

Gly Thr Leu Glu Phe Arg Thr Tyr Met Phe Leu Asn Val Phe Glu Tyr
                245                 250                 255

Val Ser Ile Trp Ser Leu Phe Lys Tyr Gln Ser Leu Leu Val Ser Ser
            260                 265                 270

Gly Ala Asn Leu Tyr Ala Ser Gly Ser Gly Pro Gln Gln Thr Gln Ser
        275                 280                 285

Phe Thr Ser Gln Asp Trp Pro Phe Leu Tyr Ser Leu Phe Gln Val Asn
    290                 295                 300

Ser Asn Tyr Val Leu Asn Gly Phe Ser Gly Ala Arg Leu Ser Asn Thr
305                 310                 315                 320

Phe Pro Asn Ile Gly Gly Leu Pro Gly Ser Thr Thr Thr His Ala Leu
                325                 330                 335
```

```
Leu Ala Ala Arg Val Asn Tyr Ser Gly Gly Ile Ser Ser Gly Asp Ile
                340                 345                 350

Gly Ala Ser Pro Phe Asn Gln Asn Phe Asn Cys Ser Thr Phe Leu Pro
            355                 360                 365

Pro Leu Leu Thr Pro Phe Val Arg Ser Trp Leu Asp Ser Gly Ser Asp
        370                 375                 380

Arg Glu Gly Val Ala Thr Val Thr Asn Trp Gln Thr Glu Ser Phe Glu
385                 390                 395                 400

Thr Thr Leu Gly Leu Arg Ser Gly Ala Phe Thr Ala Arg Gly Asn Ser
                405                 410                 415

Asn Tyr Phe Pro Asp Tyr Phe Ile Arg Asn Ile Ser Gly Val Pro Leu
            420                 425                 430

Val Val Arg Asn Glu Asp Leu Arg Arg Pro Leu His Tyr Asn Glu Ile
        435                 440                 445

Arg Asn Ile Ala Ser Pro Ser Gly Thr Pro Gly Gly Ala Arg Ala Tyr
    450                 455                 460

Met Val Ser Val His Asn Arg Lys Asn Asn Ile His Ala Val His Glu
465                 470                 475                 480

Asn Gly Ser Met Ile His Leu Ala Pro Asn Asp Tyr Thr Gly Phe Thr
                485                 490                 495

Ile Ser Pro Ile His Ala Thr Gln Val Asn Asn Gln Thr Arg Thr Phe
            500                 505                 510

Ile Ser Glu Lys Phe Gly Asn Gln Gly Asp Ser Leu Arg Phe Glu Gln
        515                 520                 525

Asn Asn Thr Thr Ala Arg Tyr Thr Leu Arg Gly Asn Gly Asn Ser Tyr
    530                 535                 540

Asn Leu Tyr Leu Arg Val Ser Ser Ile Gly Asn Ser Thr Ile Arg Val
545                 550                 555                 560

Thr Ile Asn Gly Arg Val Tyr Thr Ala Thr Asn Val Asn Thr Thr Thr
                565                 570                 575

Asn Asn Asp Gly Val Asn Asp Asn Gly Ala Arg Phe Ser Asp Ile Asn
            580                 585                 590

Ile Gly Asn Val Val Ala Ser Ser Asn Ser Asp Val Pro Leu Asp Ile
        595                 600                 605

Asn Val Thr Phe Asn Ser Gly Thr Gln Phe Asp Leu Met Asn Thr Met
    610                 615                 620

Leu Val Pro Thr Asn Ile Ser Pro Leu Tyr
625                 630

<210> SEQ ID NO 13
<211> LENGTH: 51
<212> TYPE: PRT
<213> ORGANISM: Oryza sativa
<220> FEATURE:
<221> NAME/KEY: TRANSIT
<222> LOCATION: (1)..(51)
<223> OTHER INFORMATION: CTP from OS- 1-deoxy-D-xyulose-5-Phosphate
      Synthase

<400> SEQUENCE: 13

Met Ala Leu Thr Thr Phe Ser Ile Ser Arg Gly Gly Phe Val Gly Ala
1               5                   10                  15

Leu Pro Gln Glu Gly His Phe Ala Pro Ala Ala Glu Leu Ser Leu
                20                  25                  30

His Lys Leu Gln Ser Arg Pro His Lys Ala Arg Arg Ser Ser Ser
            35                  40                  45
```

Ser Ile Ser
    50

<210> SEQ ID NO 14
<211> LENGTH: 57
<212> TYPE: PRT
<213> ORGANISM: Oryza sativa
<220> FEATURE:
<221> NAME/KEY: TRANSIT
<222> LOCATION: (1)..(57)
<223> OTHER INFORMATION: CTP from OS- Superoxide dismutase

<400> SEQUENCE: 14

Met Gln Ala Ile Leu Ala Ala Met Ala Ala Gln Thr Leu Leu Phe
1               5                   10                  15

Ser Ala Thr Ala Pro Pro Ala Ser Leu Phe Gln Ser Pro Ser Ser Ala
                20                  25                  30

Arg Pro Phe His Ser Leu Arg Leu Ala Ala Gly Pro Ala Gly Ala Ala
            35                  40                  45

Ala Ala Arg Ala Leu Val Val Ala Asp
    50                  55

<210> SEQ ID NO 15
<211> LENGTH: 44
<212> TYPE: PRT
<213> ORGANISM: Oryza sativa
<220> FEATURE:
<221> NAME/KEY: TRANSIT
<222> LOCATION: (1)..(44)
<223> OTHER INFORMATION: CTP from OS- soluble starch synthase

<400> SEQUENCE: 15

Met Ala Ala Ala Ala Val Ser Ser Leu Leu Ala Pro Ser Gly Ser Cys
1               5                   10                  15

Tyr Ser Pro Gly Cys His Ser Cys Trp Gly Pro Gly Pro Gly Gly Gly
                20                  25                  30

Arg Arg Leu Pro Ser Pro Arg Arg Pro Ile Thr
            35                  40

<210> SEQ ID NO 16
<211> LENGTH: 49
<212> TYPE: PRT
<213> ORGANISM: Oryza sativa
<220> FEATURE:
<221> NAME/KEY: TRANSIT
<222> LOCATION: (1)..(49)
<223> OTHER INFORMATION: CTP from OS- NADP dependent Malic acid enzyme

<400> SEQUENCE: 16

Met Leu Ser Ala Arg Ala Ala Ala Thr Ala Ala Ala Ala Ala Ala Ser
1               5                   10                  15

Pro Leu Trp Lys Arg Gly Glu Gly Gly Ser Ser Gly Ser Gly Ser Gly
                20                  25                  30

Cys Thr Ser Cys Arg Glu Val Arg Arg Ala Ala Ala Val Arg Val
            35                  40                  45

Arg

<210> SEQ ID NO 17
<211> LENGTH: 54
<212> TYPE: PRT
<213> ORGANISM: Oryza sativa
<220> FEATURE:
<221> NAME/KEY: TRANSIT
<222> LOCATION: (1)..(54)

```
<223> OTHER INFORMATION: CTP from OS-Phospho-2-dehydro-3-deoxyheptonate
      Aldolase 2

<400> SEQUENCE: 17

Met Ala Leu Ala Thr Asn Ser Ala Ala Val Ser Gly Gly Ala Ala Ala
1               5                   10                  15

Ala Ala Ser Ser Ala Pro Gln Pro Arg Leu Ala Ala Thr Phe Leu Pro
                20                  25                  30

Met Arg Arg Arg Thr Val Ser Ala Val His Ala Asp Pro Ala Lys
            35                  40                  45

Ser Asn Gly Pro Val Gln
    50

<210> SEQ ID NO 18
<211> LENGTH: 42
<212> TYPE: PRT
<213> ORGANISM: Oryza sativa
<220> FEATURE:
<221> NAME/KEY: TRANSIT
<222> LOCATION: (1)..(42)
<223> OTHER INFORMATION: CTP from OS- L-Ascorbate Peroxidase 5

<400> SEQUENCE: 18

Met Ala Val Val His Arg Ile Leu Arg Arg Gly Leu Ser Ala Ala Ser
1               5                   10                  15

Pro Leu Pro Ser Leu Arg Gly Leu Leu Val Ser Pro Gln Glu Leu
                20                  25                  30

Gly Arg Arg Pro Ala Ser Ser Ser Ser Ser
            35                  40

<210> SEQ ID NO 19
<211> LENGTH: 56
<212> TYPE: PRT
<213> ORGANISM: Oryza sativa
<220> FEATURE:
<221> NAME/KEY: TRANSIT
<222> LOCATION: (1)..(56)
<223> OTHER INFORMATION: CTP from OS- Phosphoglucan water dikinase

<400> SEQUENCE: 19

Met Thr Ser Leu Arg Pro Leu Glu Thr Ser Leu Ser Ile Gly Gly Arg
1               5                   10                  15

Pro Arg Arg Gly Leu Val Leu Pro Pro Pro Gly Val Gly Ala Gly Val
                20                  25                  30

Leu Leu Arg Arg Gly Ala Met Ala Leu Pro Gly Arg Arg Gly Phe Ala
            35                  40                  45

Cys Arg Gly Arg Ser Ala Ala Ser
    50                  55

<210> SEQ ID NO 20
<211> LENGTH: 47
<212> TYPE: PRT
<213> ORGANISM: Zea mays
<220> FEATURE:
<221> NAME/KEY: TRANSIT
<222> LOCATION: (1)..(47)
<223> OTHER INFORMATION: CTP from ZM- ssRUBISCO

<400> SEQUENCE: 20

Met Ala Pro Thr Val Met Met Ala Ser Ser Ala Thr Ala Val Ala Pro
1               5                   10                  15

Phe Gln Gly Leu Lys Ser Thr Ala Ser Leu Pro Val Ala Arg Arg Ser
                20                  25                  30
```

```
Ser Arg Ser Leu Gly Asn Val Ser Asn Gly Gly Arg Ile Arg Cys
        35                  40                  45
```

<210> SEQ ID NO 21
<211> LENGTH: 54
<212> TYPE: PRT
<213> ORGANISM: Zea mays
<220> FEATURE:
<221> NAME/KEY: TRANSIT
<222> LOCATION: (1)..(54)
<223> OTHER INFORMATION: CTP from ZM- beta-glucosidase

<400> SEQUENCE: 21

```
Met Ala Pro Leu Leu Ala Ala Ala Met Asn His Ala Ala Ala His Pro
1               5                   10                  15

Gly Leu Arg Ser His Leu Val Gly Pro Asn Asn Glu Ser Phe Ser Arg
            20                  25                  30

His His Leu Pro Ser Ser Ser Pro Gln Ser Ser Lys Arg Arg Cys Asn
        35                  40                  45

Leu Ser Phe Thr Thr Arg
    50
```

<210> SEQ ID NO 22
<211> LENGTH: 40
<212> TYPE: PRT
<213> ORGANISM: Zea mays
<220> FEATURE:
<221> NAME/KEY: TRANSIT
<222> LOCATION: (1)..(40)
<223> OTHER INFORMATION: CTP from ZM- Malate dehydrogenase (NADP)

<400> SEQUENCE: 22

```
Met Gly Leu Ser Thr Val Tyr Ser Pro Ala Gly Pro Arg Leu Val Pro
1               5                   10                  15

Ala Pro Leu Gly Arg Cys Arg Ser Ala Gln Pro Arg Arg Pro Arg Arg
            20                  25                  30

Ala Pro Leu Ala Thr Val Arg Cys
        35                  40
```

<210> SEQ ID NO 23
<211> LENGTH: 53
<212> TYPE: PRT
<213> ORGANISM: Zea mays
<220> FEATURE:
<221> NAME/KEY: TRANSIT
<222> LOCATION: (1)..(53)
<223> OTHER INFORMATION: CTP from ZM- Thioredoxin M-type

<400> SEQUENCE: 23

```
Met Ala Met Glu Thr Cys Phe Arg Ala Trp Ala Leu His Ala Pro Ala
1               5                   10                  15

Gly Ser Lys Asp Arg Leu Leu Val Gly Asn Leu Val Leu Pro Ser Lys
            20                  25                  30

Arg Ala Leu Ala Pro Leu Ser Val Gly Arg Val Ala Thr Arg Arg Pro
        35                  40                  45

Arg His Val Cys Gln
    50
```

<210> SEQ ID NO 24
<211> LENGTH: 17
<212> TYPE: PRT
<213> ORGANISM: Oryza sativa
<220> FEATURE:

```
<221> NAME/KEY: domain
<222> LOCATION: (1)..(17)
<223> OTHER INFORMATION: Amino acids 1-17 of OS-1-deoxy-D-xyulose-5-
      Phosphate Synthase CTP, N-terminal domain of CTP1

<400> SEQUENCE: 24

Met Ala Leu Thr Thr Phe Ser Ile Ser Arg Gly Gly Phe Val Gly Ala
1               5                   10                  15

Leu

<210> SEQ ID NO 25
<211> LENGTH: 10
<212> TYPE: PRT
<213> ORGANISM: Zea mays
<220> FEATURE:
<221> NAME/KEY: domain
<222> LOCATION: (1)..(10)
<223> OTHER INFORMATION: amino acids 18-27 of ZM-ssRUBISCO CTP, central
      domain of CTP1

<400> SEQUENCE: 25

Gln Gly Leu Lys Ser Thr Ala Ser Leu Pro
1               5                   10

<210> SEQ ID NO 26
<211> LENGTH: 29
<212> TYPE: PRT
<213> ORGANISM: Zea mays
<220> FEATURE:
<221> NAME/KEY: domain
<222> LOCATION: (1)..(29)
<223> OTHER INFORMATION: Amino acids 28-56 of ZM- beta-glucosidase CTP,
      C-terminal domain of CTP1

<400> SEQUENCE: 26

Asn Asn Glu Ser Phe Ser Arg His His Leu Pro Ser Ser Pro Gln
1               5                   10                  15

Ser Ser Lys Arg Arg Cys Asn Leu Ser Phe Thr Thr Arg
                20                  25

<210> SEQ ID NO 27
<211> LENGTH: 17
<212> TYPE: PRT
<213> ORGANISM: Zea mays
<220> FEATURE:
<221> NAME/KEY: domain
<222> LOCATION: (1)..(17)
<223> OTHER INFORMATION: Amino acids 1-17 of ZM- Malate dehydrogenase
      CTP, N-terminal domain of CTP2

<400> SEQUENCE: 27

Met Gly Leu Ser Thr Val Tyr Ser Pro Ala Gly Pro Arg Leu Val Pro
1               5                   10                  15

Ala

<210> SEQ ID NO 28
<211> LENGTH: 10
<212> TYPE: PRT
<213> ORGANISM: Oryza sativa
<220> FEATURE:
<221> NAME/KEY: domain
<222> LOCATION: (1)..(10)
<223> OTHER INFORMATION: Amino acids 18-27 of OS- Superoxide dismutase
      CTP, Central domain of CTP2

<400> SEQUENCE: 28

Pro Ala Ser Leu Phe Gln Ser Pro Ser Ser
```

```
                    1               5                         10

<210> SEQ ID NO 29
<211> LENGTH: 25
<212> TYPE: PRT
<213> ORGANISM: Oryza sativa
<220> FEATURE:
<221> NAME/KEY: domain
<222> LOCATION: (1)..(25)
<223> OTHER INFORMATION: Amino acids 28-52 of OS- soluble starch
      synthase CTP, C-terminal domain of CTP2

<400> SEQUENCE: 29

Gly Cys His Ser Cys Trp Gly Pro Gly Pro Gly Gly Gly Arg Arg Leu
1               5                   10                  15

Pro Ser Pro Arg Arg Arg Pro Ile Thr
            20                  25

<210> SEQ ID NO 30
<211> LENGTH: 17
<212> TYPE: PRT
<213> ORGANISM: Oryza sativa
<220> FEATURE:
<221> NAME/KEY: domain
<222> LOCATION: (1)..(17)
<223> OTHER INFORMATION: Amino acids 1-17 of OS- NADP dependent Malic
      acid enzyme CTP, N-terminal domain of CTP3

<400> SEQUENCE: 30

Met Leu Ser Ala Arg Ala Ala Ala Thr Ala Ala Ala Ala Ala Ala Ser
1               5                   10                  15

Pro

<210> SEQ ID NO 31
<211> LENGTH: 10
<212> TYPE: PRT
<213> ORGANISM: Oryza sativa
<220> FEATURE:
<221> NAME/KEY: domain
<222> LOCATION: (1)..(10)
<223> OTHER INFORMATION: Amino acids 18-27 of OS-Phospho-2-dehydro-3-
      deoxyheptonate Aldolase 2 CTP, Central domain of CTP3

<400> SEQUENCE: 31

Pro Gln Pro Arg Leu Ala Ala Thr Phe Leu
1               5                   10

<210> SEQ ID NO 32
<211> LENGTH: 27
<212> TYPE: PRT
<213> ORGANISM: Zea mays
<220> FEATURE:
<221> NAME/KEY: domain
<222> LOCATION: (1)..(27)
<223> OTHER INFORMATION: Amino acids 28-54 of ZM- Thioredoxin M-type,
      C-terminal domain of CTP3

<400> SEQUENCE: 32

Val Leu Pro Ser Lys Arg Ala Leu Ala Pro Leu Leu Ser Val Gly Arg
1               5                   10                  15

Val Ala Thr Arg Arg Pro Arg His Val Cys Gln
            20                  25

<210> SEQ ID NO 33
<211> LENGTH: 9
<212> TYPE: PRT
<213> ORGANISM: Zea mays
```

```
<220> FEATURE:
<221> NAME/KEY: domain
<222> LOCATION: (1)..(9)
<223> OTHER INFORMATION: Amino acids 1-9 of ZM- Malate dehydrogenase
      CTP, portion of N-terminal domain of CTP4

<400> SEQUENCE: 33

Met Gly Leu Ser Thr Val Tyr Ser Pro
1               5

<210> SEQ ID NO 34
<211> LENGTH: 12
<212> TYPE: PRT
<213> ORGANISM: Oryza sativa
<220> FEATURE:
<221> NAME/KEY: domain
<222> LOCATION: (1)..(12)
<223> OTHER INFORMATION: Amino acids 10-21 of OS- NADP dependent Malic
      acid enzyme CTP, portion of N-terminal domain of CTP4

<400> SEQUENCE: 34

Ala Ala Ala Ala Ala Ala Ser Pro Pro Gln Pro Arg
1               5                   10

<210> SEQ ID NO 35
<211> LENGTH: 6
<212> TYPE: PRT
<213> ORGANISM: Zea mays
<220> FEATURE:
<221> NAME/KEY: domain
<222> LOCATION: (1)..(6)
<223> OTHER INFORMATION: Amino acids 22-27 of ZM- ssRUBISCO CTP, Central
      domain of CTP4

<400> SEQUENCE: 35

Ser Thr Ala Ser Leu Pro
1               5

<210> SEQ ID NO 36
<211> LENGTH: 10
<212> TYPE: PRT
<213> ORGANISM: Oryza sativa
<220> FEATURE:
<221> NAME/KEY: domain
<222> LOCATION: (1)..(10)
<223> OTHER INFORMATION: Amino acids 28-37 of OS- soluble starch
      synthase CTP, portion of C-terminal domain of CTP4

<400> SEQUENCE: 36

Gly Cys His Ser Cys Trp Gly Pro Gly Pro
1               5                   10

<210> SEQ ID NO 37
<211> LENGTH: 17
<212> TYPE: PRT
<213> ORGANISM: Zea mays
<220> FEATURE:
<221> NAME/KEY: domain
<222> LOCATION: (1)..(17)
<223> OTHER INFORMATION: amino acids 38-54 of zm-Thioredoxin M-type,
      portion of C-terminal domain of CTP4

<400> SEQUENCE: 37

Leu Leu Ser Val Gly Arg Val Ala Thr Arg Arg Pro Arg His Val Cys
1               5                   10                  15

Gln

<210> SEQ ID NO 38
```

```
<211> LENGTH: 9
<212> TYPE: PRT
<213> ORGANISM: Oryza sativa
<220> FEATURE:
<221> NAME/KEY: domain
<222> LOCATION: (1)..(9)
<223> OTHER INFORMATION: amino acids 1-9 of zm-malate dehydrogenase
      CTP, portion of N-terminal domain of CTP5

<400> SEQUENCE: 38

Met Gly Leu Ser Thr Val Tyr Ser Pro
1               5

<210> SEQ ID NO 39
<211> LENGTH: 8
<212> TYPE: PRT
<213> ORGANISM: Oryza sativa
<220> FEATURE:
<221> NAME/KEY: domain
<222> LOCATION: (1)..(8)
<223> OTHER INFORMATION: amino acids 10-17 of os-NADP dependent Malic
      acid enzyme CTP, portion of N-terminal domain of CTP5

<400> SEQUENCE: 39

Ala Ala Ala Ala Ala Ala Ser Pro
1               5

<210> SEQ ID NO 40
<211> LENGTH: 4
<212> TYPE: PRT
<213> ORGANISM: Oryza sativa
<220> FEATURE:
<221> NAME/KEY: domain
<222> LOCATION: (1)..(4)
<223> OTHER INFORMATION: amino acids 18-21 of os-L-Ascorbate Peroxidase
      5 CTP, portion of central domain of CTP5

<400> SEQUENCE: 40

Pro Ser Leu Arg
1

<210> SEQ ID NO 41
<211> LENGTH: 6
<212> TYPE: PRT
<213> ORGANISM: Zea mays
<220> FEATURE:
<221> NAME/KEY: domain
<222> LOCATION: (1)..(6)
<223> OTHER INFORMATION: amino acids 22-27 of zm-ssRUBISCO CTP, portion
      of central domain of CTP5

<400> SEQUENCE: 41

Ser Thr Ala Ser Leu Pro
1               5

<210> SEQ ID NO 42
<211> LENGTH: 12
<212> TYPE: PRT
<213> ORGANISM: Oryza sativa
<220> FEATURE:
<221> NAME/KEY: domain
<222> LOCATION: (1)..(12)
<223> OTHER INFORMATION: amino acids 28-39 of os-superoxide dismutase
      CTP, portion of C-terminal domain of CTP5

<400> SEQUENCE: 42

Ala Arg Pro Phe His Ser Leu Arg Leu Ala Ala Gly
1               5                   10
```

-continued

```
<210> SEQ ID NO 43
<211> LENGTH: 13
<212> TYPE: PRT
<213> ORGANISM: Oryza sativa
<220> FEATURE:
<221> NAME/KEY: domain
<222> LOCATION: (1)..(13)
<223> OTHER INFORMATION: amino acids 40-52 of os-phophoglucan water
      dikinase, portion of C-terminal domain of CTP5

<400> SEQUENCE: 43

Arg Arg Gly Phe Ala Cys Arg Gly Arg Ser Ala Ala Ser
1               5                   10

<210> SEQ ID NO 44
<211> LENGTH: 45
<212> TYPE: PRT
<213> ORGANISM: Artificial Sequence
<220> FEATURE:
<223> OTHER INFORMATION: synthetic construct; ADP-glucose synthase 1 CTP

<400> SEQUENCE: 44

Met Gln Phe Ala Leu Ala Leu Asp Thr Asn Ser Gly Pro His Gln Ile
1               5                   10                  15

Arg Ser Cys Glu Gly Asp Gly Ile Asp Arg Leu Glu Lys Leu Ser Ile
            20                  25                  30

Gly Gly Arg Lys Gln Glu Lys Ala Leu Arg Asn Arg Cys
        35                  40                  45

<210> SEQ ID NO 45
<211> LENGTH: 47
<212> TYPE: PRT
<213> ORGANISM: Artificial Sequence
<220> FEATURE:
<223> OTHER INFORMATION: synthetic construct; ADP-glucose synthetase CTP

<400> SEQUENCE: 45

Met Gln Phe Ser Ser Val Leu Pro Leu Glu Gly Lys Ala Cys Met Ser
1               5                   10                  15

Pro Val Arg Arg Gly Ser Gly Gly Tyr Gly Ser Glu Arg Met Arg Ile
            20                  25                  30

Asn Cys Cys Ser Ile Arg Arg Asn Lys Ala Leu Arg Arg Met Cys
        35                  40                  45

<210> SEQ ID NO 46
<211> LENGTH: 54
<212> TYPE: PRT
<213> ORGANISM: Artificial Sequence
<220> FEATURE:
<223> OTHER INFORMATION: synthetic construct; Dihydrodipicolinate
      synthase CTP

<400> SEQUENCE: 46

Met Ile Ser Pro Thr Asn Leu Leu Pro Ala Arg Lys Ile Thr Pro Val
1               5                   10                  15

Ser Asn Gly Gly Ala Ala Thr Ala Ser Pro Ser Ser Pro Ser Val Ala
            20                  25                  30

Ala Arg Pro Arg Arg Leu Pro Ser Gly Leu Gln Ser Val Thr Gly Arg
        35                  40                  45

Gly Lys Val Ser Leu Ala
    50

<210> SEQ ID NO 47
<211> LENGTH: 49
```

```
<212> TYPE: PRT
<213> ORGANISM: Artificial Sequence
<220> FEATURE:
<223> OTHER INFORMATION: synthetic construct; DXP reductoisomerase (Os)

<400> SEQUENCE: 47

Met Ala Leu Lys Val Val Ser Phe Pro Gly Asp Leu Ala Ala Val Ser
1               5                   10                  15

Phe Leu Asp Ser Asn Arg Gly Gly Ala Phe Asn Gln Leu Lys Val Asp
            20                  25                  30

Leu Pro Phe Gln Thr Arg Asp Arg Arg Ala Val Ser Leu Arg Arg Thr
        35                  40                  45

Cys

<210> SEQ ID NO 48
<211> LENGTH: 52
<212> TYPE: PRT
<213> ORGANISM: Artificial Sequence
<220> FEATURE:
<223> OTHER INFORMATION: synthetic construct; Ferredoxin-1 CTP

<400> SEQUENCE: 48

Met Ala Thr Val Leu Gly Ser Pro Arg Ala Pro Ala Phe Phe Phe Ser
1               5                   10                  15

Ser Ser Ser Leu Arg Ala Ala Pro Ala Pro Thr Ala Val Ala Leu Pro
            20                  25                  30

Ala Ala Lys Val Gly Ile Met Gly Arg Ser Ala Ser Ser Arg Arg Arg
        35                  40                  45

Leu Arg Ala Gln
    50

<210> SEQ ID NO 49
<211> LENGTH: 51
<212> TYPE: PRT
<213> ORGANISM: Artificial Sequence
<220> FEATURE:
<223> OTHER INFORMATION: synthetic construct; Glutamine synthetase CTP

<400> SEQUENCE: 49

Met Ala Gln Ala Val Val Pro Ala Met Gln Cys Arg Val Gly Val Lys
1               5                   10                  15

Ala Ala Ala Gly Arg Val Trp Ser Ala Gly Arg Thr Arg Thr Gly Arg
            20                  25                  30

Gly Gly Ala Ser Pro Gly Phe Lys Val Met Ala Val Ser Thr Gly Ser
        35                  40                  45

Thr Gly Val
    50

<210> SEQ ID NO 50
<211> LENGTH: 43
<212> TYPE: PRT
<213> ORGANISM: Artificial Sequence
<220> FEATURE:
<223> OTHER INFORMATION: synthetic construct; OsALS1

<400> SEQUENCE: 50

Met Ala Thr Thr Ala Ala Ala Ala Ala Ala Leu Ser Ala Ala Ala
1               5                   10                  15

Thr Ala Lys Thr Gly Arg Lys Asn His Gln Arg His His Val Leu Pro
            20                  25                  30

Ala Arg Gly Arg Val Gly Ala Ala Ala Val Arg
```

<210> SEQ ID NO 51
<211> LENGTH: 47
<212> TYPE: PRT
<213> ORGANISM: Artificial Sequence
<220> FEATURE:
<223> OTHER INFORMATION: synthetic construct; OsFBPase

<400> SEQUENCE: 51

Met Ala Ala Ala Ala Thr Thr Ser Ser His Leu Leu Leu Leu Ser Arg
1               5                   10                  15

Gln Gln Ala Ala Ala Ser Leu Gln Cys Gly Leu Ser Phe Arg Arg Gln
            20                  25                  30

Pro Gly Arg Leu Ala Gly Gly Ser Ser Ala Pro Ser Val Arg Cys
        35                  40                  45

<210> SEQ ID NO 52
<211> LENGTH: 59
<212> TYPE: PRT
<213> ORGANISM: Artificial Sequence
<220> FEATURE:
<223> OTHER INFORMATION: synthetic construct; OsTRX-M

<400> SEQUENCE: 52

Met Ala Leu Glu Thr Cys Phe Arg Ala Trp Ala Thr Leu His Ala Pro
1               5                   10                  15

Gln Pro Pro Ser Ser Gly Gly Ser Arg Asp Arg Leu Leu Leu Ser Gly
            20                  25                  30

Ala Gly Ser Ser Gln Ser Lys Pro Arg Leu Ser Val Ala Ser Pro Ser
        35                  40                  45

Pro Leu Arg Pro Ala Ser Arg Phe Ala Cys Gln
    50                  55

<210> SEQ ID NO 53
<211> LENGTH: 47
<212> TYPE: PRT
<213> ORGANISM: Artificial Sequence
<220> FEATURE:
<223> OTHER INFORMATION: synthetic construct; Ribulose bisphosphate
    carboxylase small chain (Os)

<400> SEQUENCE: 53

Met Ala Pro Ser Val Met Ala Ser Ser Ala Thr Thr Val Ala Pro Phe
1               5                   10                  15

Gln Gly Leu Lys Ser Thr Ala Gly Met Pro Val Ala Arg Arg Ser Gly
            20                  25                  30

Asn Ser Ser Phe Gly Asn Val Ser Asn Gly Gly Arg Ile Arg Cys
        35                  40                  45

<210> SEQ ID NO 54
<211> LENGTH: 53
<212> TYPE: PRT
<213> ORGANISM: Artificial Sequence
<220> FEATURE:
<223> OTHER INFORMATION: synthetic construct; Ribulose bisphosphate
    carboxylase/oxygenase CTP

<400> SEQUENCE: 54

Met Ala Ala Ala Phe Ser Ser Thr Val Gly Ala Pro Ala Ser Thr Pro
1               5                   10                  15

Thr Arg Ser Ser Phe Leu Gly Lys Lys Leu Asn Lys Pro Gln Val Ser
            20                  25                  30

```
Ala Ala Val Thr Tyr His Gly Lys Ser Ser Ser Asn Ser Arg Phe
        35                  40                  45

Lys Ala Met Ala Ala
    50

<210> SEQ ID NO 55
<211> LENGTH: 56
<212> TYPE: PRT
<213> ORGANISM: Artificial Sequence
<220> FEATURE:
<223> OTHER INFORMATION: synthetic construct; Starch branching enzyme
      IIB CTP

<400> SEQUENCE: 55

Met Ala Phe Arg Val Ser Gly Ala Val Leu Gly Gly Ala Val Arg Ala
1               5                   10                  15

Pro Arg Leu Thr Gly Gly Gly Glu Gly Ser Leu Val Phe Arg His Thr
            20                  25                  30

Gly Leu Phe Leu Thr Arg Gly Ala Arg Val Gly Cys Ser Gly Thr His
        35                  40                  45

Gly Ala Met Arg Ala Ala Ala Ala
    50                  55

<210> SEQ ID NO 56
<211> LENGTH: 57
<212> TYPE: PRT
<213> ORGANISM: Artificial Sequence
<220> FEATURE:
<223> OTHER INFORMATION: synthetic construct; unnamed protein product
      CTP

<400> SEQUENCE: 56

Met Gly Leu Ser Thr Val Tyr Ser Pro Ala Gly Pro Arg Leu Val Pro
1               5                   10                  15

Ala Pro Leu Gly Arg Cys Arg Ser Ala Gln Pro Arg Arg Pro Arg Arg
            20                  25                  30

Ala Pro Leu Ala Thr Val Arg Cys Ser Val Asp Ala Thr Lys Gln Ala
        35                  40                  45

Gln Asp Gly Val Ala Thr Ala Val Ala
    50                  55
```